(12) United States Patent
Darji et al.

(10) Patent No.: US 7,115,269 B2
(45) Date of Patent: Oct. 3, 2006

(54) **ATTENUATED *SALMONELLA* STRAIN USED AS A VEHICLE FOR ORAL IMMUNIZATION**

(75) Inventors: Ayub Darji, Braunschweig (DE); Carlos A. Guzman, Braunschweig (DE); Kenneth Timmis, Braunschweig (DE); Siegfried Weiss, Braunschweig (DE); Birgit Gerstel, Braunschweig (DE); Trinad Chakraborty, Braunschweig (DE); Petra Wachholz, Braunschweig (DE); Jürgen Wehland, Braunschweig (DE)

(73) Assignee: Gesellschaft fuer Biotechnologische Forschung mbH (GBF), Braunschweig (DE)

( * ) Notice: Subject to any disclaimer, the term of this patent is extended or adjusted under 35 U.S.C. 154(b) by 0 days.

(21) Appl. No.: 09/419,545

(22) Filed: Oct. 18, 1999

(65) Prior Publication Data

US 2003/0180320 A1 Sep. 25, 2003

Related U.S. Application Data

(63) Continuation-in-part of application No. PCT/EP97/06933, filed on Dec. 11, 1997.

(30) Foreign Application Priority Data

Apr. 18, 1997 (DE) ................................ 97 106 503

(51) Int. Cl.
| | |
|---|---|
| *A61K 39/02* | (2006.01) |
| *A61K 48/00* | (2006.01) |
| *A61K 39/112* | (2006.01) |
| *A61K 39/00* | (2006.01) |
| *A01N 63/00* | (2006.01) |
| *C12N 15/00* | (2006.01) |
| *C12P 21/04* | (2006.01) |

(52) U.S. Cl. .............................. 424/200.1; 424/93.48; 424/93.2; 424/234.1; 424/258.1; 424/184.1; 435/320.1; 435/71.1; 435/69.3

(58) Field of Classification Search ............. 424/93.48, 424/93.4, 93.1, 200.1, 184.1, 234.1, 258.1, 424/230.1; 435/71.2, 71.1, 69.3, 320.1; 935/72
See application file for complete search history.

(56) References Cited

U.S. PATENT DOCUMENTS

| | | | | |
|---|---|---|---|---|
| 5,231,176 A | * | 7/1993 | Goeddel et al. ......... 435/69.51 |
| 5,332,658 A | * | 7/1994 | Dyall-Smith et al. .......... 435/5 |
| 5,656,488 A | * | 8/1997 | Curtiss, III et al. ..... 435/252.33 |
| 5,736,388 A | * | 4/1998 | Chada et al. ............ 435/320.1 |
| 5,824,538 A | * | 10/1998 | Branstrom et al. ....... 435/252.1 |
| 5,869,057 A | * | 2/1999 | Rock ....................... 424/192.1 |
| 5,877,159 A | | 3/1999 | Powell et al. ................ 514/44 |
| 5,986,061 A | * | 11/1999 | Pestka ........................ 530/352 |
| 6,054,570 A | * | 4/2000 | Vogelstein et al. ......... 536/23.4 |
| 6,099,848 A | * | 8/2000 | Frankel et al. ........... 424/246.1 |
| 6,150,170 A | | 11/2000 | Powell et al. ................ 435/455 |
| 6,365,576 B1 | * | 4/2002 | Carr ............................ 514/44 |
| 6,682,729 B1 | | 1/2004 | Powell et al. .............. 424/93.2 |
| 2003/0153527 A1 | | 8/2003 | Powell et al. ................. 514/44 |

FOREIGN PATENT DOCUMENTS

WO   WO 97/08955   3/1997

OTHER PUBLICATIONS

Mitcehll et al. Mol. Microbiol. 5: 1883-1888, 1991.*
Feldman et al. Am. J. Respir. Cell Mol. Biol. 5: 416-423, 1991.*
Bowie et al. Science 247: 1306-1310, 1990.*
Houghton et al. Vaccines86, Cold-Spring Harbor Laboratory, p. 21-25, 1986.*
Srinivasan et al. Biol. Reproduct. 53: 462-471, 1995.*
Brown et al. J. Infect. Dis. 155: 86-92, 1987.*
Yang et al. J. Immunol. 145: 2281-2285, 1990.*
Tite et al. Immunology 70: 540-546, 1990.*
Verma et al. Vaccine 13: 142-150, 1996.*
Fouts et al. Vaccine 13: 1697-1705, 1995.*
Sztein et al. J. Immunol. 155: 1697-1705, 1995, abstract.*
Stocker et al. Intern. Rev. Immunol. 11: 167-178, 1994.*
"An Attenuated *aroA Salmonella typhimurium* Vaccine Elicits Humoral and Cellular Immunity to Cloned β-Galactosidase in Mice", Brown et al., XP-002071286, The Journal of Infectious Diseases, vol. 155, No. 1, Jan. 1987, pp. 86-92.
"*Salmonella typhimurium* ΔaroA ΔaroD Mutants Expressing a Foreign Recombinant Protein Induce Specific Major Histocompatibility Complex Class I-Restricted Cytotoxic T Lymphocytes in Mice", Turner et al., XP-002071285, Infection and Immunity, December 1993, pp. 5374-5380.
"Attenuated *Shigella* as a DNA Delivery Vehicle for DNA-Mediated Immunization", Sizemore et al., Science, vol. 270, Oct. 13, 1995, pp. 299-302.
"Interaction of *Salmonella typhi* Strains with Cultured Human Monocyte-Derived Marcophages", Sizemore, et al., XP-002071319, Infection and Immunity, Jan. 1997, pp. 309-312.
International Preliminary Examination Report for PCT/EP97/06933 dated Jul. 2, 1999.
International Search Report in PCT/EP97/06933 dated Jul. 28, 1998.

(Continued)

*Primary Examiner*—S. Devi
(74) *Attorney, Agent, or Firm*—Marshall, Gerstein & Borun LLP

(57) ABSTRACT

The present invention is directed to an attenuated *Salmonella* comprising a eukaryotic expression vector for delivery of the eukaryotic expression vector to a eukaryotic cell. Delivery may be to eukaryotic cells cultured in vitro or to cells in vivo, such as by oral administration of the attenuated *Salmonella* comprising the eukaryotic expression vector.

15 Claims, 24 Drawing Sheets

OTHER PUBLICATIONS

"Expression in *Escherichia coli* and Sequence Analysis of the Listeriolysin O Determinant of *Listeria monocytogenes*", Mengaud et al., Infection and Immunity, Apr. 1998, pp. 766-772.

"A Novel Bacterial Virulence Gene in *Listeria monocytogenes* Required for Host Cell Microfilament Interaction with Homology to the Proline-Rich Region of Vinculin", Domann et al., The EMBO Journal vol. 11, No. 5, 1992, pp. 1981-1990.

"Gene Transfer from Bacteria to Mammalian Cells", Courvalin et al., Comptes Rendues de L'Academie Des Sciences, vol. 318, No. 12, 1995, pp. 1207-1212.

"Oral Somatic Transgene Vaccination Using Attenuated *S. typhimurium*", Darji et al., Cell, vol. 91, Dec. 12, 1997, pp. 765-775.

Bouwer et al., "Listeriolysin O is a target of the immune response to *Listeria monocytogense*," *J. Exp. Med.*, 175:1467-1471, 1992.

Ikonomidis et al., "Delivery of a viral antigen to the Class I processing and presentation pathway by *Listeria monocytogense*," *J. Exp. Med.* 180:2209-2218, 1994.

Pamer et al., "Precise prediction of a dominant class I MHC-restrict epitope of *Listeria monocytogense*," *Nature* 353:852-855, 1991.

Safley et al., "Role of listeriolysin-O (LLO) in the T lymphocyte response to infection with *Listeria monocytogense*," *J. Immunol.* 146:3604-3616, 1991.

* cited by examiner

US 7,115,269 B2

ATTENUATED *SALMONELLA* STRAIN USED AS A VEHICLE FOR ORAL IMMUNIZATION

This is a continuation-in-part of International Application No. PCT/EP97/06933 filed Dec. 11, 1997, the entire disclosure of which is incorporated herein by reference.

BACKGROUND OF INVENTION

The design of efficient vaccines against infectious diseases remains a major challenge in medical science. Low cost, non-invasive administration, life-long protection by single doses combined with ease of preparation, storage and transport are desirable goals to be achieved. In this respect, live attenuated bacterial carriers that express heterologous antigens are attractive vehicles for the oral delivery of vaccines. This type of delivery should result in a broad spectrum of both mucosal and systemic immune responses. Use of vaccine vectors overcomes some of the limitation of oral delivery of proteins, which usually need to be co-administered with adjuvant proteins such as cholera toxin to evoke an immune response (Brown et al., 1987; Flynn et al, 1990). In addition, administration of live replicating vectors might be advantageous over other forms of administration such as microencapsulation because of the immunomodulatory properties of cell wall components of bacteria. Finally, the natural route of entry could prove to be of benefit since many bacteria like *Salmonella* egress from the gut lumen via M cells into Peyer's Patches (Jones et al, 1994; Neutra et al, 1996; Siebers and Finley, 1996) and migrate eventually into lymph nodes and spleen, thus allowing targeting of vaccines to inductive sites of the immune system.

Genetic immunization has recently provided a promising new approach to the vaccination problem (for review see Donnelly et al., 1997). Isolated plasmid DNA—introduced into muscle or skin of the host—leads to expression of antigen in the host cells when transcription is driven by eukaryotic control elements. This has led to B and T cell stimulation and to protective responses. How these responses are generated remains still unclear. Muscle cells apparently express low levels of MHC class I but lack MHC class II and costimulatory molecules. Although, it is not known which cells function as antigen presenting cells (APC) under these circumstances, it is likely that resident dendritic cells or macrophages capture the antigen and migrate to lymph nodes and spleen to stimulate $CD4^+$ and $CD8^+$ T cells. Indeed antigen expressing dendritic cells have been observed after genetic immunization into the skin using a gene gun (Condon et al., 1996). It is not known whether DNA is also transferred directly into dendritic cells when plasmids are applied into muscles.

Several advantages have been observed with genetic immunization over conventional vaccination. The DNA can be detected for a considerable period of time thus acting like a depot of antigen (Ning et al, 1993). Sequence motifs in some plasmids are immunostimulatory and can function as adjuvant (Krieg et al., 1995; Messina et al., 1991; Yamamoto et al., 1992). Co-expression of cytokines enhance the response and offer the possibility of modulating the induction of an immune response into a desired direction (Zhignan et al, 1995; Geissler et al, 1997; Kim et al, 1997). However, several obstacles need to be overcome before general applicability can be achieved.

If it would be possible to deliver plasmids for genetic immunization with an attenuated bacterial carrier, the advantages and versatility of both systems would be combined. In addition, the natural route of administration would deliver DNA to cell types which have specifically evolved to induce immune responses. *Salmonella* spp. are particularly suited for this purpose because of the extensive knowledge on the genetics and physiology of many strains. A large body of documentation exists on their utility as heterologous antigen carriers that are capable of inducing protective immune responses (Fairwether et al., 1990; Molina et al., 1990; Newton et al., 1989; reviewed Chatfield et al, 1994; Roberts et al, 1994). Also, safe attenuated strains of *Salmonella* are available and are already in use as vaccines in animal husbandry and man (Hassan, 1996; Steinbach, 1996; Fox, 1997; Germanier and Fürer, 1975). Finally, recombinant plasmids constructed in laboratory strains of *E. coli* can be directly introduced into *Salmonellae* without further manipulations.

SUMMARY OF THE INVENTION

An attenuated strain of *Salmonella typhimurium* has been used as a vehicle for oral genetic immunization. Eukaryotic expression vectors containing the genes for b-galactosidase, or truncated forms of ActA and listeriolysin—two virulence factors of *Listeria monocytogenes*—that were controlled by an eukaryotic promoter have been used to transform a *S. typhimurium* aroA strain. Multiple or even single immunizations with these transformants induced a strong cytotoxic and helper T cell response as well as an excellent antibody response. Multiple immunizations with listeriolysin transformants protected the mice completely against a lethal challenge of *L. Monocytogenes*. Partial protection was already observed with a single dose. ActA appeared not to be a protective antigen.

The strength and the kinetics of the response suggested that the heterologous antigens were expressed within the eukaryotic host cells following transfer of plasmid DNA from the bacterial carrier strain. Transfer of plasmid DNA could be unequivocally shown in vitro using primary peritoneal macrophage. The demonstration of RNA splice products and expression of β-galactosidase in the presence of tetracycline—an inhibitor of bacterial protein synthesis—indicated that the gene was expressed by host cells rather than bacteria. Oral genetic immunization with *Salmonella* carriers provides a highly versatile system for antigen delivery, represents a potent system to identify candidate protective antigens for vaccination, and will permit efficacious generation of antibodies against virtually any DNA segment encoding an open reading frame.

According to one embodiment the invention concerns an attenuated *Salmonella* strain carrying an eucaryotic expression vector for the expression of a heterologous gene or gene fragment or an autologous gene or gene fragment comprised by the vector within an open reading frame, wherein the attenuation is adjusted to a vaccination of vertebrates including humans.

The *Salmonella* strain according to the invention can be a *S. typhimurium* strain, especially *S. typhimurium* aroA SL 7207 or *S. typhimurium* LT2 and preferably aroA544 (ATCC 335).

Further, the *Salmonella* strain according to the invention can be a *S. typhi* strain, especially *S. typhi* Ty21a.

According to the invention *Salmonella* strains are comprised, wherein the eucaryotic expression vector is or can be derived from the known plasmid pCMVβ which comprises the structural gene of β-galactosidase (β-gal)
under the control of the human cytomegalovirus (CMV) immediate early promoter comprised by the plasmid pCMVβ per se and includes
a splice donor,
two splice acceptor sites in between the promoter and the β-galactosidase gene, and facultatively
the polyadenylation site of SV40.

The *Salmonella* strain according to the invention can be characterized by a heterologous gene or an autologous gene coding for a protein and especially an immunogenic protein or protective antigen.

According to the invention *Salmonella* strains are comprised wherein the heterologous gene is selected from the group consisting of
the *Escherichia coli*-β-galactosidase gene (lacZ-gene),
a non-hemolytic truncated variant of the *Listeria monocytogenes*—listeriolysine gene (hly gene) and
a truncated variant of the *Listeria monocytogenes*—actA gene (actA gene).

Another embodiment of the invention concerns a vaccine for oral, nasal, mucosal, intravenous, intraperitonal, intradermal, or subcutaneous gene delivery to vertebrates including humans, wherein the vaccine comprises a *Salmonella* strain according to the invention.

Further, another embodiment of the invention concerns a use of a *Salmonella* strain according to the invention or of a vaccine according to the invention for expression screening of heterologous genomic DNA libraries or genomic cDNA libraries by DNA vaccination in vertebrates including humans.

Finally, another embodiment of the invention concerns a process for the recovery of
(i) an attenuated *Salmonella* strain carrying an eucaryotic expression vector for the expression of a heterologous gene or gene fragment or an autologous gene or gene fragment comprised by the vector within an open reading frame, wherein the attenuation is adjusted to a vaccination of vertebrates including humans; or
(ii) a vaccine for oral, nasal, mucosal, intravenous, intraperitonal, intradermal, or subcutaneous gene delivery to vertebrates including humans, wherein the vaccine comprises a *Salmonella* strain according to (i) or
(iii) an immunogenic protein or protective antigen as expression product of an eucaryotic expression vector according to (i), characterized by
(a) using genetic information from a heterologous or autologous DNA or cDNA library as gene fragment or gene to be expressed by an eucaryotic expression vector carried by an attenuated *Salmonella* strain, wherein the attenuation is adjusted to a vaccination of vertebrates including humans,
(b) carrying out a DNA vaccination by means of the attenuated *Salmonella* strain according to (a) in a vertebrate or human being,
(c) carrying out an expression screening for an expression product of a gene or gene fragment according to (a) providing an immune response
(d) and recovering a *Salmonella* strain according to the invention or of a vaccine according to the invention or of an immunogenic protein or protective antigen providing an immune response in vertebrates including humans.

To sum up, we report that orally administered *S. typhimurium* aroA carrying plasmids encoding β-galactosidase (β-gal) of *Escherichia coli,* or truncated forms of ActA or listeriolysin of *Listeria monocytogenes* under the control of an eukaryotic promoter induce an efficient humoral and cellular immune response. The strength and kinetics of the response is only compatible with the interpretation of a transfer of the expression plasmid from the *Salmonella* carrier to the nucleus of APC of the host. β-galactosidase activity was detectable even five weeks after administration of the oral vaccine. In addition, in vitro experiments with mouse primary macrophages demonstrated an efficient transfer of plasmid DNA from attenuated bacteria into the nucleus of phagocytic host cells.

Results

To achieve genetic immunization with a live attenuated bacterial carrier three plasmids were used which are based on the commercially available plasmid pCMVβ. This plasmid contains the structural gene of β-gal under the control of the human cytomegalovirus (CMV) immediate early promoter and includes a splice donor and two splice acceptor sites in between the promoter and the structural gene. For studies examining the efficiency of the immune response against pathogens the β-gal gene was replaced by genes encoding two virulence factors of *Listeria monocytogenes*. A truncated gene encoding a non-hemolytic variant of listeriolysin (pCMVhly) from amino acid positions 26 to 482 and a truncated variant of the structural gene of the membrane protein (pCMVactA) encoding amino acid 31–613 were used. *S. typhimurium* aroA strain SL7207 was transformed with these three plasmids and groups of mice were orally immunized by feeding $10^8$ organisms to each mouse per immunization. This dose was found to be optimal (data not shown). The mice did not show any overt signs of illness using this immunization schedule.

Induction of a Strong T Cell Response by Immunization with *Salmonellae* Carrying Eukaryotic Expression Vectors The working hypothesis of these experiments is that orally administered *S. typhimurium* aroA would result in uptake of the bacteria by macrophages and/or dendritic cells, with concomitant activation by the endotoxin of the bacteria. Following a few rounds of bacterial division the intracellular bacteria would die because of their inability to synthesize essential aromatic amino acids. During this process plasmids would be released and transferred into the cytosol and the nucleus of the infected cells. Eventually, the encoded genes will be expressed by host APC.

The first prediction of this hypothesis is the induction of a strong cytotoxic response of CD8 T cells, since antigen would be expressed in the cytosol, the cellular compartment responsible for MHC class I presentation. To this end, two kinds of experiments were performed. Mice were either infected orally once with recombinant *Salmonellae* and their cytotoxic T cell responses were followed for several weeks by testing their spleen cells directly ex vivo (data not shown) or after one restimulation in vitro. Alternatively, mice were orally immunized four times at two weeks intervals and the course of the cytotoxic response was examined. FIG. 1 demonstrates that a strong and specific CD8 T cell response can be elicited with orally administered *Salmonella* carrying eukaryotic expression plasmids. Mice immunized with the truncated gene of listeriolysin elicited only a response towards targets sensitized with the immunodominant peptide comprising AA91-99 of listeriolysin (LLO) and not against targets sensitized with soluble hen egg lysozyme (HEL) or a control peptide (FIG. 1A). Similarly, spleen cells from mice immunized with *Salmonella* carrying the ActA expression plasmid could only respond to ActA (FIG. 1D). To reveal the cytotoxic response against ActA, we exploited the pore-forming activity of listeriolysin. This activity of listeriolysin allows the introduction of soluble passenger proteins into the cytosol of target cells (Darji et al., 1995a; Darji et al., 1997). Stimulators and target cells were therefore sensitized with a mixture of soluble ActA and LLO. A specific response was observed only when the combination of ActA and LLO was used. No response was found when LLO alone was tested. These responses were specific for the plasmid encoded antigen during the whole time period indicated in FIG. 1 panels B & C and E & F and were also observed when the response of mice immunized with *Salmonella* harboring the β-gal control plasmid was studied (data not shown).

The kinetic of the responses indicated that even a single dose elicited a strong cytotoxic T cell response which peaked 5 weeks after immunization and then slowly declined (FIGS. 1C and F). On the other hand, the response was still rising even at the end of the observation period, i.e. 5 weeks after the last challenge in mice that had received four immunizing doses (FIGS. 1B and E). Thus, a strong cytotoxic response was observed when using *Salmonella* as potential vehicle for genetic immunization.

Genetic immunization usually also evokes a CD4 helper T cell response (Donnelly et al., 1997). Therefore, cells from spleen and mesenteric lymph nodes of the same mice used above were tested for their proliferative response against soluble proteins. This type of response is mainly due to presentation of antigen via MHC class II molecules and carried out by CD4 T cells. As shown in FIG. 2, a strong and specific helper T cell response, in parallel to the cytotoxic response is observed when eukaryotic expression plasmids carried by *Salmonellae* were used for immunization (FIGS. 2A and D). As with the CD8 response, a single dose was sufficient for a good response which was still increasing at the end of the observation period regardless of whether listeriolysin or ActA was used as antigen (FIGS 2C and F). Four consecutive immunizations however, resulted in an even stronger response which appeared long lasting since the response apparently was still increasing five weeks after the last challenge (FIGS. 2B and E). Similar results were obtained with *Salmonella* carrying the control plasmid expressing β-gal (data not shown). Analysis of the supernatants of the in vitro cultures revealed production of IFNγ by these T cells. No IL-4 could be found, suggesting that such an immunization scheme is mainly inducing a TH1 or inflammatory type of T helper response.

Induction of Specific Antibodies by Immunization with *Salmonellae* Carrying Eukaryotic Expression Vectors Pooled sera of the groups of mice used above were tested for the presence of specific antibodies. Clearly, in addition to a cytotoxic and helper T cell response, immunization with *Salmonellae* carrying eukaryotic expression plasmids induced strong and specific antibody responses as revealed by ELISA (FIGS. 3A and B) or immunoblot (data not shown). Again a single immunization was sufficient for a good response which peaked four weeks after the administration of the bacteria and then declined in the same way as seen for cytotoxic response (FIGS. 3A and B). Four immunizations did not increase the antibody titer significantly but probably induced a longer lasting response since a plateau of antibody titer was not reached even at the end of the observation period (FIGS. 3A and B).

The analysis of the subclass distribution of individual mice at week 11 indicated a high concentration of IgG2a while the concentration of IgG2b and IgG3 was negligible (FIGS. 3C and D). This is in agreement with the finding that only IFNγ and no IL-4 could be detected in the supernatant of the restimulated T helper cells. However, IgG1 was also observed at high concentrations in the immune sera. This subclass is found when TH2 helper cells are taking part in the immune response, indicating that under our experimental conditions TH2 cells might also be induced but were not revealed in the in vitro T cell assay. In addition, IgA antibodies were evoked by this immunization schedule (not shown).

Taken together the results presented in FIG. 1–3 show that immunization with *S. typhimurium* aroA carrying eukaryotic expression vectors can evoke responses in all three specific effector compartments of the immune system, namely, cytotoxic CD8 T cell, CD4 T cells and antibodies. The response in the T helper compartment was strongly biased towards a TH1 or inflammatory T helper response.

Protection Against Lethal Doses of *L. monocytogenes*

The strong response observed, in particular that of cytotoxic T cells, suggested that mice immunized in such a way should be protected from a lethal dose of *L monocytogenes*. Therefore, 90 days after the first immunization or 48 days after the fourth immunization—where applicable—mice were challenged i. v. with a dose of bacteria corresponding to $10 \times LD_{50}$. FIG. 4 shows that animals which were immunized four times consecutively with *Salmonella* e harboring an eukaryotic expression vector that encodes truncated LLO were completely protected (FIG. 4A). Animals that had received a single vaccination only were partially but significantly protected since at the time of termination of that experiment 60% of the animals were still alive. All animals that were immunized with *Salmonellae* that carried the β-gal control plasmid were not protected and died within four days. Surprisingly, immunizations with *Salmonellae* carrying the ActA expression plasmid did not result in protection, although strong cytotoxic and helper T cell responses could be demonstrated in mice from the same group indicating that the immunization had been successfull (data not shown). Thus, the listerial membrane protein ActA is not a protective antigen.

Evidence for Transfer of the Expression Plasmid from the Carrier *Salmonellae* to Host Cells in vivo We were concerned that a weak activity of the eukaryotic promoter in the bacteria or a cryptic prokaryotic promoter in the plasmid could result in expression of the antigens in the bacterial carrier thus eliciting the potent immune response. In fact, the recombinant *Salmonellae* harboring the pCMVβ exhibited low β-gal activity (2.5 U) compared to the parental strain. To rule out any possibility, we immunized mice with a recombinant *Salmonella* strain that produced more than 100 fold higher levels (334 U) of β-gal enzymatic activity. A single vaccinating dose using these bacteria did not elicit any measurable T cell or antibody response (FIG. 5A–C). Repeated vaccination, however, resulted in a weak cytotoxic T cell response detectable after in vitro restimulation, although, it barely reached the strength of the response observed using a single immunization with *Salmonellae* harboring the eukaryotic expression plasmid of β-gal (FIG. 5A). Neither a CD4 T cell nor an antibody response was observed even after repeated oral immunization with *Salmonellae* constitutively expressing β-gal (FIGS. 5B and C).

As a result of the aroA mutation bacteria appear to die very quickly since live bacteria could never be demonstrated after immunization at various time points examined. Nevertheless, even at five weeks following oral administration of *Salmonellae* harboring the eukaryotic β-gal expression plasmid, enzymatic activity of β-gal could be detected in adherent cells—most likely macrophages—from the spleen of these mice suggesting plasmid transfer to the eucaryotic cell (data not shown). To further corroborate this observation we injected *Salmonellae* carrying the pCMVβ vector into the peritoneum of mice and harvested the peritoneal exudate cells after 1 hour. Cells were then cultured overnight in the presence of tetracycline to inhibit bacterial protein synthesis and finally stained for β-gal activity. Enzymatic activity of β-gal was observed in a large number of macrophage like cells. The staining was diffuse and clearly not restricted to the endocytic vesicles in which *Salmonella* usually reside. This suggests that plasmid DNA was transferred from dying *Salmonellae* to host cells and had occurred at a high frequency.

DNA Transfer from *S. typhimurium* aroA to Mammalian Host Cells in vitro

To obtain direct evidence that DNA transfer from the bacterial carrier to the mouse macrophages can take place, primary peritoneal macrophages were infected with *Salmonellae* harboring the β-gal expression plasmid (pCMVβ). After infection for one hour, gentamicin was added to kill remaining extracellular bacteria. Four hours later tetracycline was added to kill resident intracellular bacteria. After overnight incubation, cells were stained for β-gal activity. In up to 30% of the adherent, macrophage-like cells, enzymatic activity could be demonstrated even in the continuous presence of tetracycline which blocks bacterial protein synthesis (FIG. 6).

To show that β-galactosidase was produced by the host cell, and not by the bacteria, two type of experiments were performed. Firstly, adherent peritoneal cells were infected and treated as described above. After overnight incubation RNA was extracted. If the plasmid had indeed been transferred and transcribed in the nucleus of the host cell, RNA splice products derived from the splice donor and acceptor sites within the vector should be demonstratable. By RT-PCR with a primer pair that hybridises to sequences on either side of the small intron, a PCR product could be observed which corresponded to one of the expected splice products (FIG. 7A). The identity of this product was confirmed by DNA sequencing (data not shown).

Secondly, biosynthetic labelling of proteins in the presence of tetracycline should only allow translation of mRNA produced by the eukaryotic host cells. Adherent peritoneal cells were infected as described and were pulsed for 30 min with $^{35}$S-methionine after 4, 24 or 48 hours in the absence or presence of tetracycline. At four hours no β-gal could be observed by immunoprecipitation, even in the absence of tetracycline where bacterial products should have been labelled (FIG. 7B). Thus, transfer of plasmid DNA and eukaryotic expression had not taken place yet. However, β-gal could be immunoprecipitated following a 24 hour or 48 hour incubation period even when tetracycline was continuously present during both the incubation and labelling period. Preincubation of the anti-β-gal antibody with an excess of unlabeled β-gal demonstrated the specificity of the immunoprecipitation (FIG. 7B/lane 10). This clearly indicates that the β-gal precipitated was produced by the infected mammalian host cell itself and not by the bacterium which had originally carried the expression plasmid. Thus, a transfer of the plasmid from *Salmonellae* to the host cell must have taken place.

Discussion

The transfer of eukaryotic expression plasmids from attenuated enteric bacteria into the nucleus of host cells has recently been demonstrated. While this work was in progress it was reported that auxotropic mutants of *Shigella* and *E. coli* that express the invasin of *Shigella* can carry eukaryotic expression plasmids into host cells (Sizemore et al., 1995; Courvalin et al., 1995). Given that both bacteria are capable of escape from the phagolysosome into the cytosol of the host cell, it follows that lysis of bacteria in this compartment would allow transfer of the released plasmid into the nucleus. Transfer of plasmid from intracellular pathogens such as *Salmonella* would be harder to imagine as these bacteria are generally retained within vacuoles of the infected host cell. Indeed, only a "low efficiency" of plasmid transfer into a macrophage cell line using attenuated *Salmonella* had been reported (Sizemore et al., 1995). Our initial experiments using several macrophage cell lines had also indicated that this was indeed the case (data not shown).

However, the kinetic and strength of the immune response after administering *Salmonella* carriing euckaryotic expression vectors suggested that a plasmid transfer might have taken place in vivo. We therefore decided to investigate primary macrophages isolated from the peritoneum of mice. Using these cells we could clearly demonstrate a transfer of an eucaryotic expression plasmid vector into host cells. A pathway that permits transfer of proteins from endocytic vesicles into the cytosol of some cell types including macrophages has been described (Reis de Sousa and Germain, 1995; Norbury et al., 1995). Whether such a pathway could also be responsible for the transfer of nucleic acids obseved here remains to be studied. The fact that plasmid transfer with *Salmonella* was only observed with primary macrophages and not with cell lines suggests the presence of a transport pathway which is only operating efficiently in primary cells.

Evidence for a transfer of plasmid DNA from *Salmonella* to the host cell in vitro is compelling. Splicing of RNA and protein synthesis in the presence of tetracycline are both only possible if the gene is expressed by the eukaryotic host cell. Evidence that transfer of the expression vector in vivo is responsible for induction of the strong immune response observed, also was obtained. Enzymatic activity of β-gal could be observed five weeks after the last challenge in a few adherent spleen cells. However, viable *Salmonella* could not be detected even when tested one week after the last infection, thus, arguing that β-gal expression cannot be due to residual surviving *Salmonella*. Nevertheless, it is intriguing how such antigen expressing cells can coexist in the presence of specific cytotoxic T cells.

Strong cytotoxic and, protective responses have only been reported with *Salmonella* that secrete the antigens. No comparable responses have been described using *Salmonella* that constitutively express nonsecreted heterologous proteins (Hess et al., 1996). High doses of recombinant bacteria that express intracellular protein were required to induce CD8 T cells (Turner et al., 1993). Although induction of specific antibodies have been described under some experimental conditions (Guzman et al., 1991; Walker et al., 1992) no antibody response was observed under the circumstances described above (Turner et al., 1993). This was confirmed by our own results (FIG. 5). We therefore find it highly unlikely that the strong responses of cytotoxic and helper T cells as well as the specific antibody production is the result of a fortuitous expression of the antigens in the *Salmonella* carrier.

The strength of the immune response observed especially after a single dose of immunization indicates that transfer of DNA by bacterial carrier is probably superior to a direct application of isolated plasmid DNA into skin or muscles. This suggests that by using the natural port of entry of a pathogen, the expression vector is transferred into cell types that have evolved to efficiently induce an immune response. It is likely that the *Salmonella* carrier is taken up by macrophages and dendritic cells. Whether, macrophages play a role during stimulation of naive T cells against bacteria is not clear, but dendritic cells are known to be highly efficient in priming resting T cells. Since the antigen is expressed in the cytosol of these cells a strong cytotoxic T cell response is to be expected.

The induction of an additionally strong helper and antibody response is puzzling and can only be speculated upon. Some cytosolic proteins can efficiently be presented by MHC class II molecules (Brooks and McCluskey 1993). However, it would be a very fortunate coincidence if all three proteins used in the present study display this property. In any case, it could not explain the antibody responses that we observed. It is more likely that APC expressing the antigen are lysed by specific cytotoxic cells and dying antigen containing cells or free antigen is taken up by neighbouring APC and presented via MHC class II molecules. The generated humoral response could be explained in a similar way.

In summary, oral genetic immunization using attenuated *Salmonellae* as carrier could work as schematically depicted in FIG. 8. *Salmonella* enter the host via M cells in the intestine. The bacteria are taken up in the dome areas by phagocytic cells such as macrophages and dendritic cells. These cells are activated by the pathogen and start to differentiate and probably to migrate into lymph nodes and spleen. During this time period the bacteria die due to their attenuating mutation and liberate the plasmid-based eukaryotic expression vectors. The plasmids are then transferred into the cytosol either via a specific transport system or by endosomal leakage. Finally, the vector enters the nucleus and is transcribed, thus, leading to antigen expression in the cytosol of the host cells. Specific cytotoxic T cells are induced by these activated APC which lyse antigen expressing cells. Free antigen or dying cells can be taken up by other APC, which now in turn can stimulate helper cells. Free antigen would also be responsible for the induction of an antibody response. In addition, bacterial endotoxin and DNA sequence motifs of the vector could also function as adjuvant and could contribute to the strength of the responses observed.

The helper T cell response induced with this type of genetic immunization seemed strongly biased to the TH1 type as indicated by IFNg production of restimulated T cells in vitro and the high titer of IgG2a in the humoral response (Mosmann and Coffman, 1989). This is not unexpected since bacteria usually induce inflammatory types of response. For many vaccination strategies it is desirable to induce an TH1 response for protection against the particular pathogen, e. g. strains of mice which respond with TH2 cells against *Leishmania* major do not clear the parasite and are not protected while mice which mount a TH1 response are resistant (Sher and Coffman, 1992). On the other hand, induction of TH2 type of responses or the conversion of a TH1 response into a TH2 response has been shown to be advantageous in inflammatory autoimmune diseases (Tian et al., 1996). Similarly, infections by nematodes might also require a TH2 response (Sher and Coffman, 1992). Since the bacteria are only being used as a vehicle in transferring the expression plasmids and therefore play only a secondary role it should be possible to manipulate the TH1 response. The induction of specific IgG1 suggests the presence of a TH2 component during the helper response that might be augmentable. Co-expression of the antigen together with certain cytokines or costimulatory molecules or alternatively using antisense strategies to suppress costimulatory molecules should make it possible to drive the responses more towards TH2.

Two well characterized virulence factors were tested as antigens for protection against a lethal challenge with *L. monocytogenes*. Listeriolysin has been shown before to induce protection (Harty and Bevan, 1992; Hess et al., 1996). This was also true under our experimental conditions. Interestingly, even a single dose of *Salmonellae* harboring the eukaryotic listeriolysin expression plasmid was sufficient to afford protection to 60% of the mice. On the other hand, ActA did not serve as protective antigen. The membrane protein ActA obviously is not available to the presentation mechanisms as long as the bacteria are alive. This raises the question as to whether membrane proteins of bacteria in general are not protective or whether ActA is a special case. Extensive phosphorylation of the ActA protein by host kinases following infection may affect its ability to be processed. Nevertheless, the role of bacterial surface-bound proteins in protection can now easily be addressed using the *Salmonellae* system for genetic vaccination.

The induction of a strong and specific antibody response which can be measured in ELISA and by immunoblot revealed additional benefits derived from the type of immunization described here. Thus, to raise specific polyclonal and possibly also monoclonal antibodies, any open reading frame can be inserted into an expression plasmid and used for immunization. This will facilitate the characterization of gene products where only sequence information is available.

In conclusion: using attenuated *Salmonella* which carry eukaryotic expression vectors, genetic immunization can be achieved by oral administration of the carrier. The stimulation of cytotoxic and helper T cells as well as the induction of a strong antibody response provides a very versatile system for new immunization strategies. The strength of this approach also draws on the development of newer more rationally attenuated *Salmonellae* strains as well as technical advances in providing conditional and targeted eukaryotic expression by the infected host cell. The possibility of genetic immunization with DNA fragments containing open reading frames will allow to define the function of new gene products, provide novel serological reagents, and permit delineation and assess efficacies of protective antigens in vaccination protocols.

Now the invention is described in greater detail based on figures and experimental data.

DESCRIPTION OF THE DRAWINGS

FIG. 1 Induction of cytotoxic T cells in mice orally immunized with $10^8$ *S. typhimurium* aroA carrying eukaryotic expression plasmids which encode listeriolysin or ActA. Mice were immunized either four times with two week interval (A, B, D, E) or once (C, F) with *Salmonella* carrying pCMVhly (A–C) or pCMVActA (D–F) and spleen cells were restimulated once in vitro with a synthetic peptide comprising AA91-99 of listeriolysin (A–C) or with a mixture of purified ActA and hemolytically active listeriolysin which results in the class I presentation of ActA due to the pore-forming activity of listeriolysin (Darji et al., 1995a; Darji et al., 1997). Restimulated T cells were tested with radiolabelled P815 target cells at an effector to target ratio of 10:1.

FIG. 2 Induction of helper T cells in mice orally immunized with $10^8$ S. typhimurium aroA carrying eukaryotic expression plasmids which encode listeriolysin or ActA. Spleen (SPC) and lymph node cells (LNC) from the same mice tested for cytotoxic T cell responses displayed in FIG. 1 were tested for T helper responses. Mice were immunized either four times (A, B, D, E) or once (C, F) with Salmonella carrying pCMVhly (A–C) or pCMVActA (D, F) and restimulated in vitro. After two days proliferation was tested by incorporation of $^3$H-Thymidine.

FIG. 5 Comparison of orally induced immune responses elicited with Salmonella harboring prokaryotic or eukaryotic expression plasmids for β-gal. Mice were immunized with Salmonella haboring either the eukaryotic expression plasmid pCMVβ or the plasmid pAH97 that constitutively expressed β-gal from the Pr and Ps promotor of XylS of Pseudomonas putida. Bacteria harboring the eukaryotic vector were administered orally once (●), whereas bacteria express β-gal under the control of the prokaryotic promoter were administered either once (♦) or four times with two week intervals (▼). The arrows indicate the time of booster immunizations.

MATERIALS AND METHODS

Figure 1A:
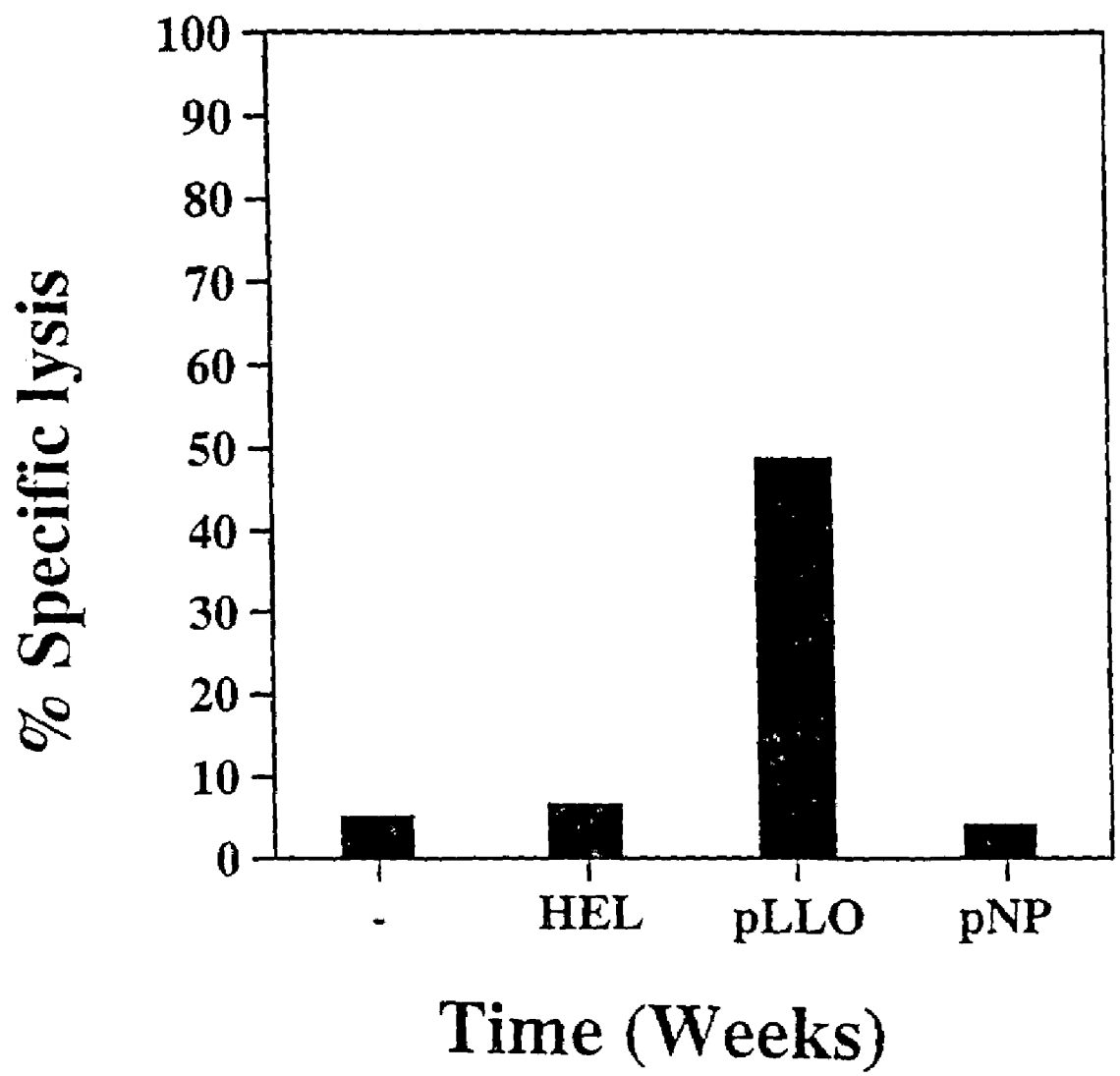
FIG. 1A. Specificity of the anti-listeriolysin cytotoxic response. Target cells were sensitized with henegglysozyme (HEL), peptide AA 91-99 of listeriolysin (pLLO) or control peptide of nucleoprotein of influenza virus (pNP). Displayed is the experiment with spleen cells from week 5 shown in panel B. Similar specificity was observed at all other time points.
Figure 1B:
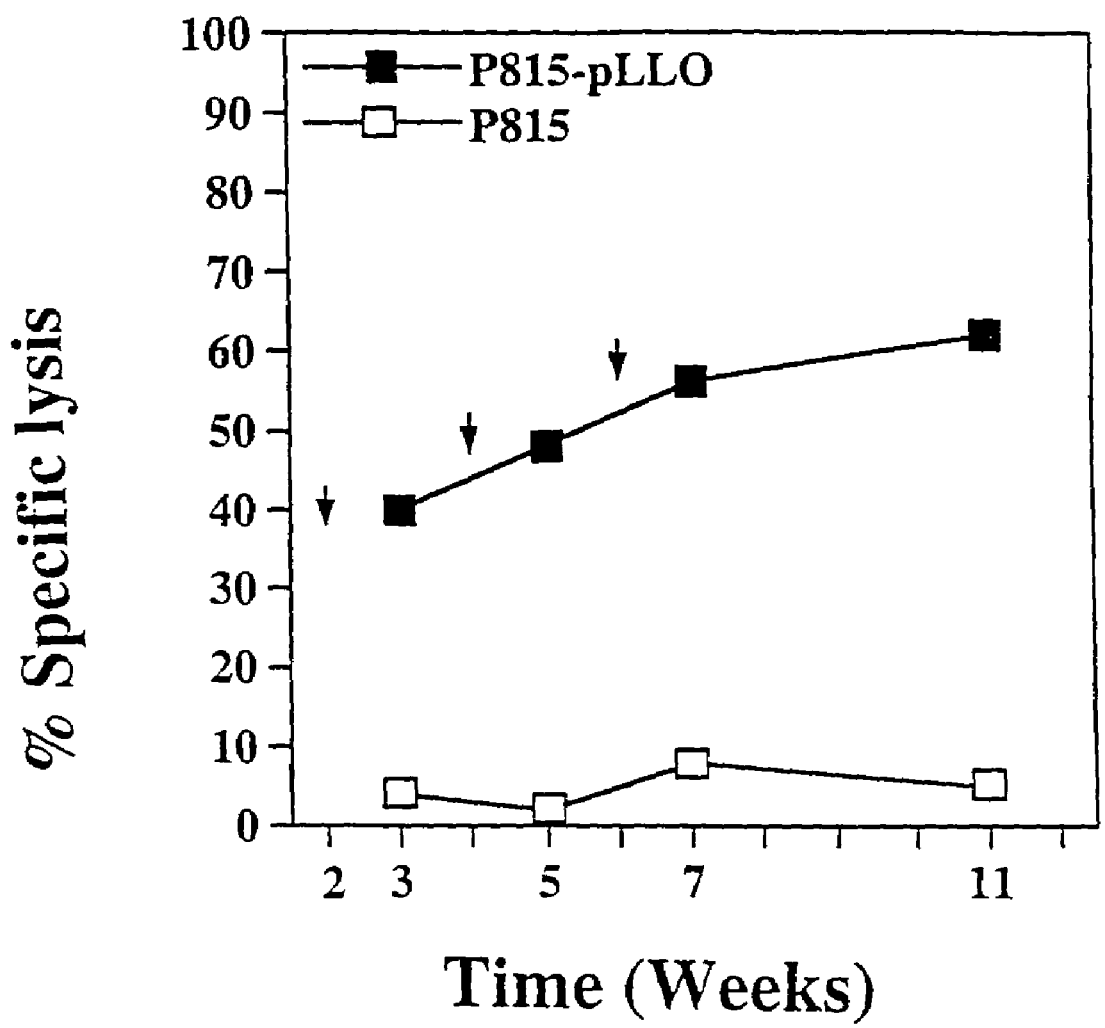
FIG. 1B. Kinetic of the cytotoxic response of mice immunized four times with pCMVhly. The arrows indicate the booster immunizations.
Figure 1C:
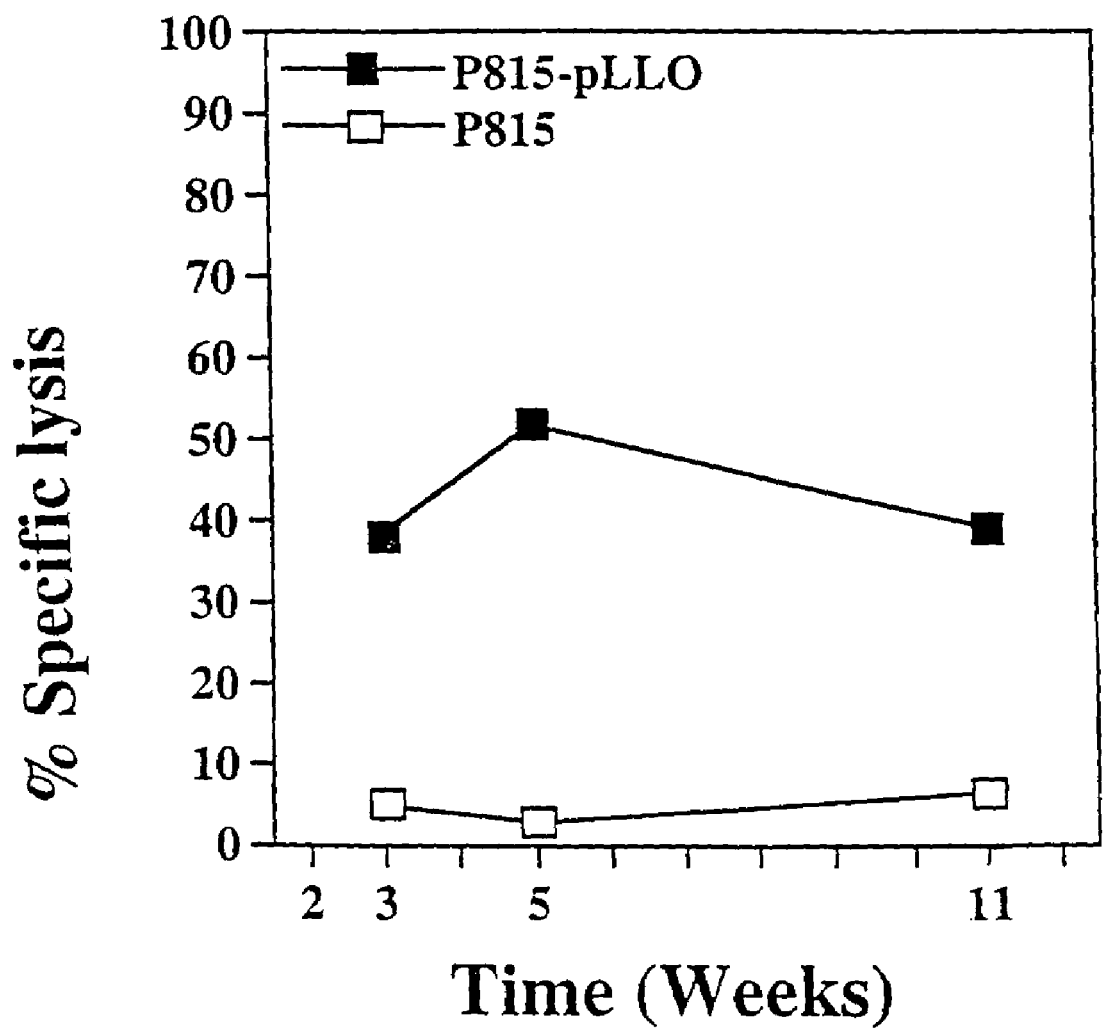
FIG 1C. Kinetic of the cytotoxic response of mice immunized once with pCMVhly.
Figure 1D:
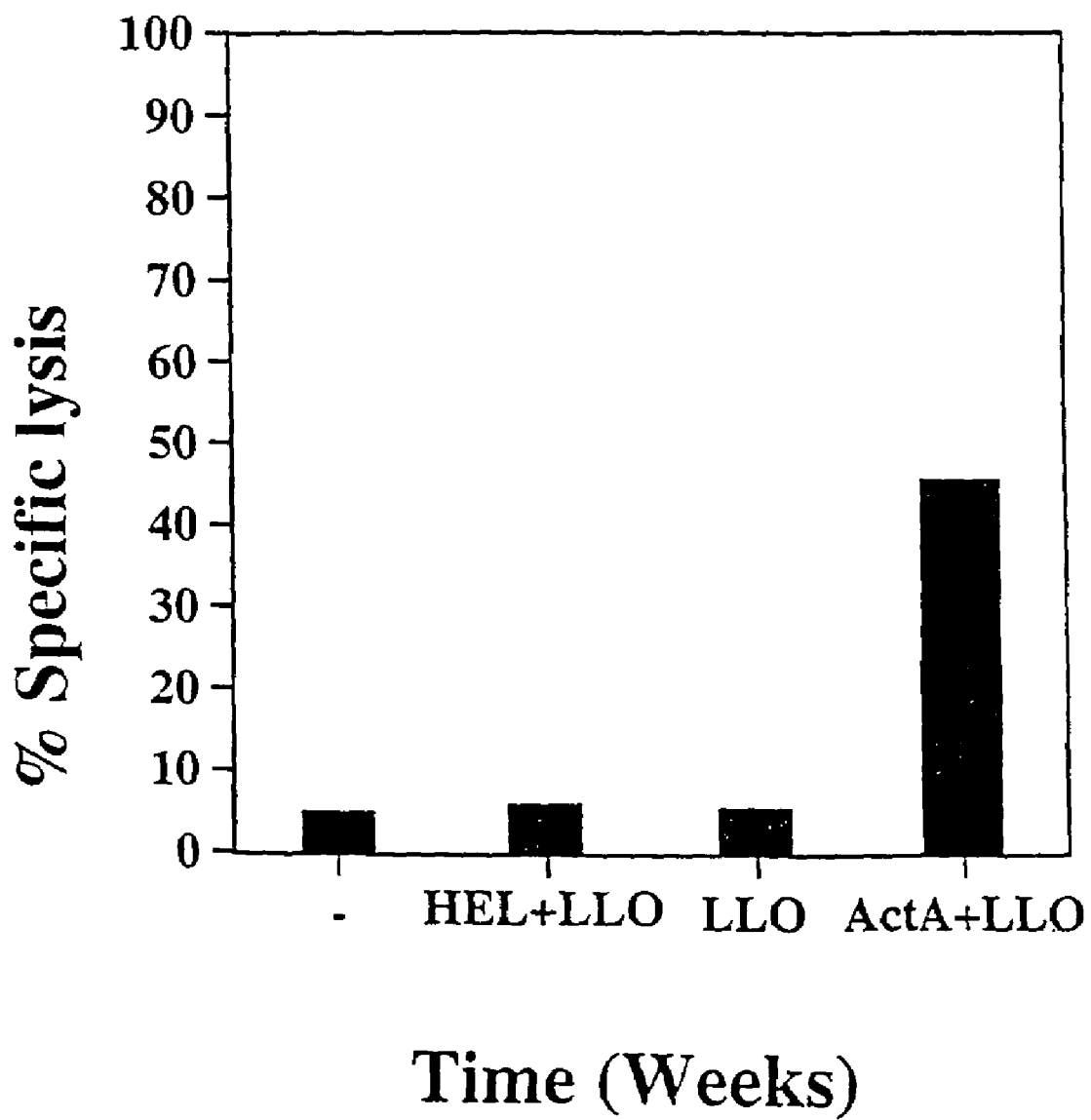
FIG. 1D. Specificity of the anti-ActA cytotoxic response. Target cells were sensitized with a mixture of ActA and listeriolysin (ActA+LLO), HEL and listeriolysin (HEL+LLO) or listeriolysin alone (LLO). Displayed is the experiment with restimulated spleen cells from week 5 shown in panel E. Similar specificity was observed at other time points and including other synthetic peptides of various sources.
Figure 1E:
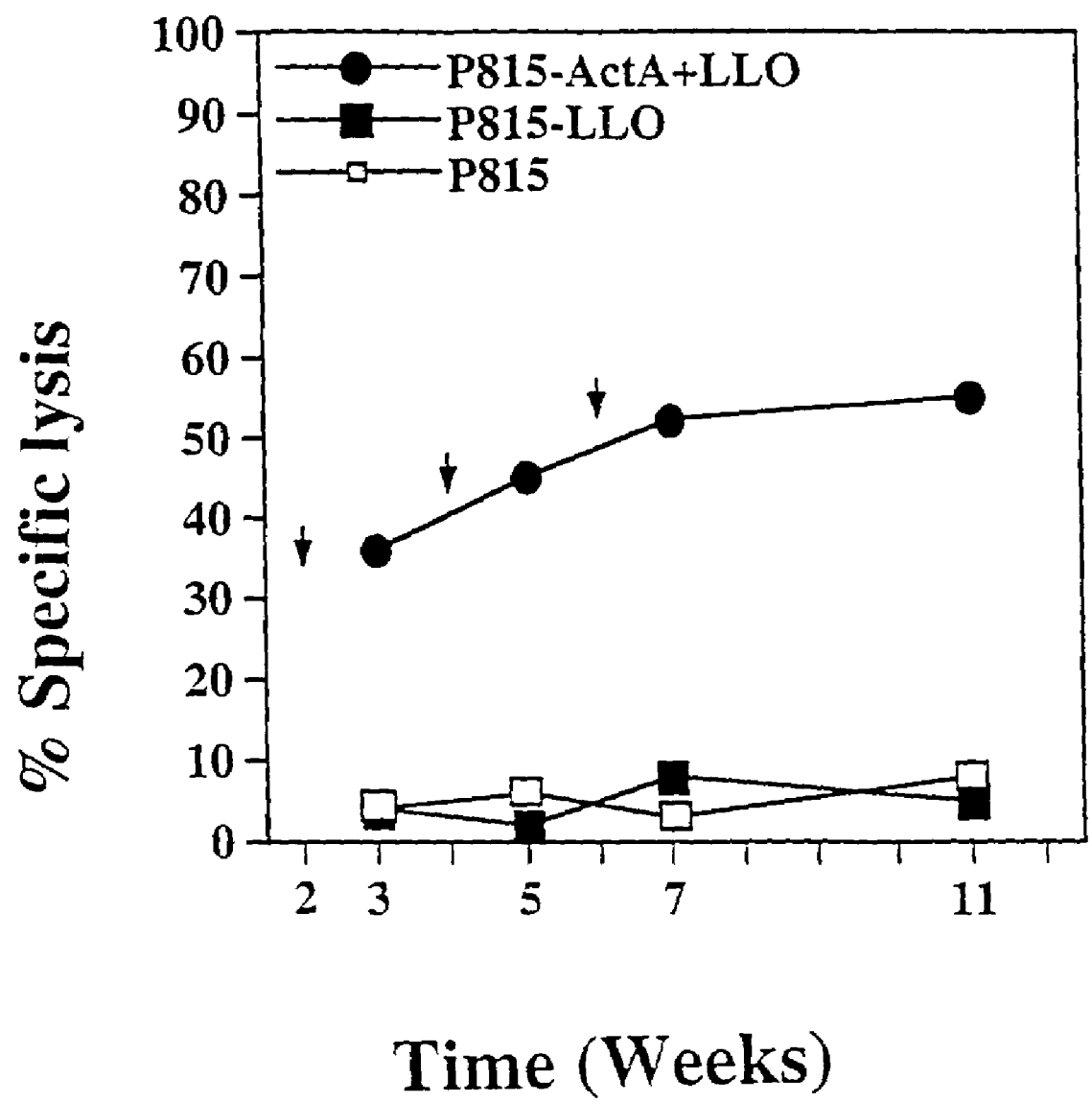
FIG. 1E. Kinetic of the cytotoxic T cell response in mice immunized four times pCMVActA. Arrows indicate booster immunizations.
Figure 1F:
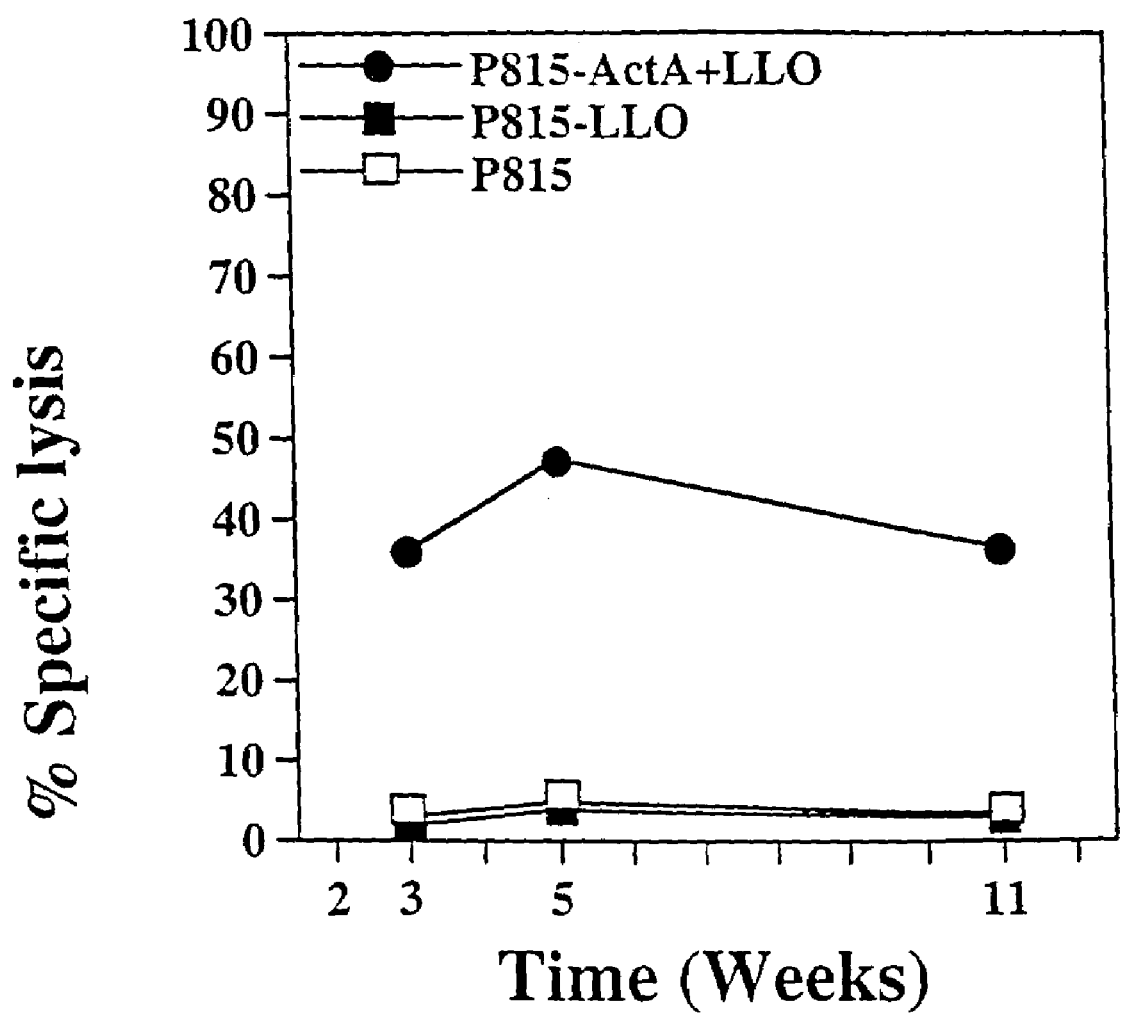
FIG. 1F. Kinetic of the cytotoxic T cell response in mice immunized once with pCMVActA. The specificity of the cytotoxic response was further assessed by testing the spleen cells of mice immunized in a similar way with pCMVβ (β-gal) on target cells sensitized with pLLO, ActA plus listeriolysin or a β-gal expressing transfectant of P815 (data not shown). Similarly, a specific cytotoxic T cell response was observed against β-gal, but the kinetic was not followed as systematically as for the two other antigens.
Figure 2A:
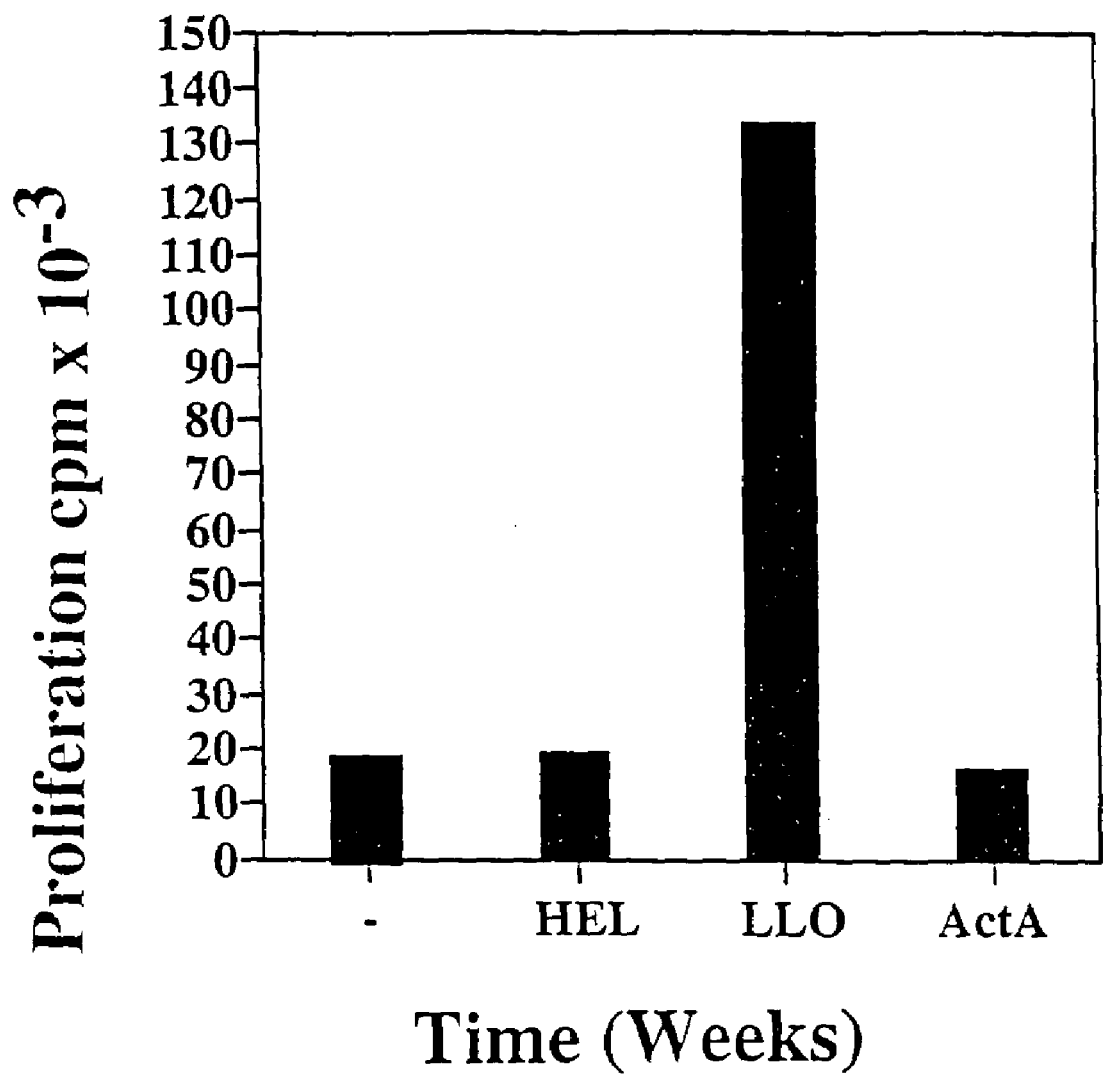
FIG. 2A: Specificity of the proliferative response of spleen cells from mice immunized with pCMVhly. T cells tested were the same as those displayed in panel B at week 11. Similar results were obtained at other time points.
Figure 2B:
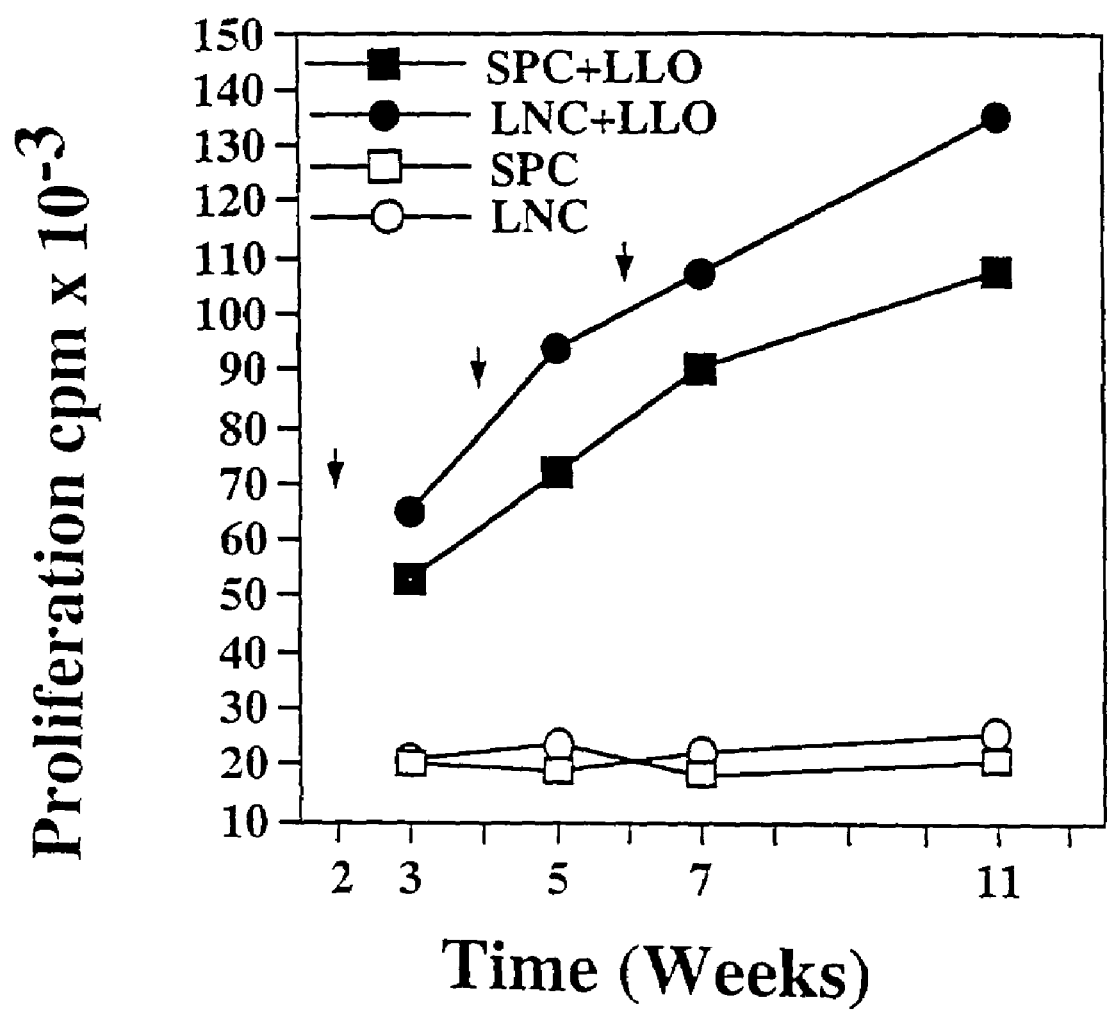
FIG. 2B: Kinetic of the proliferative response of spleen and lymph node cells from mice immunized four times with pCMVhly. Arrows indicate the booster immunizations.
Figure 2C:
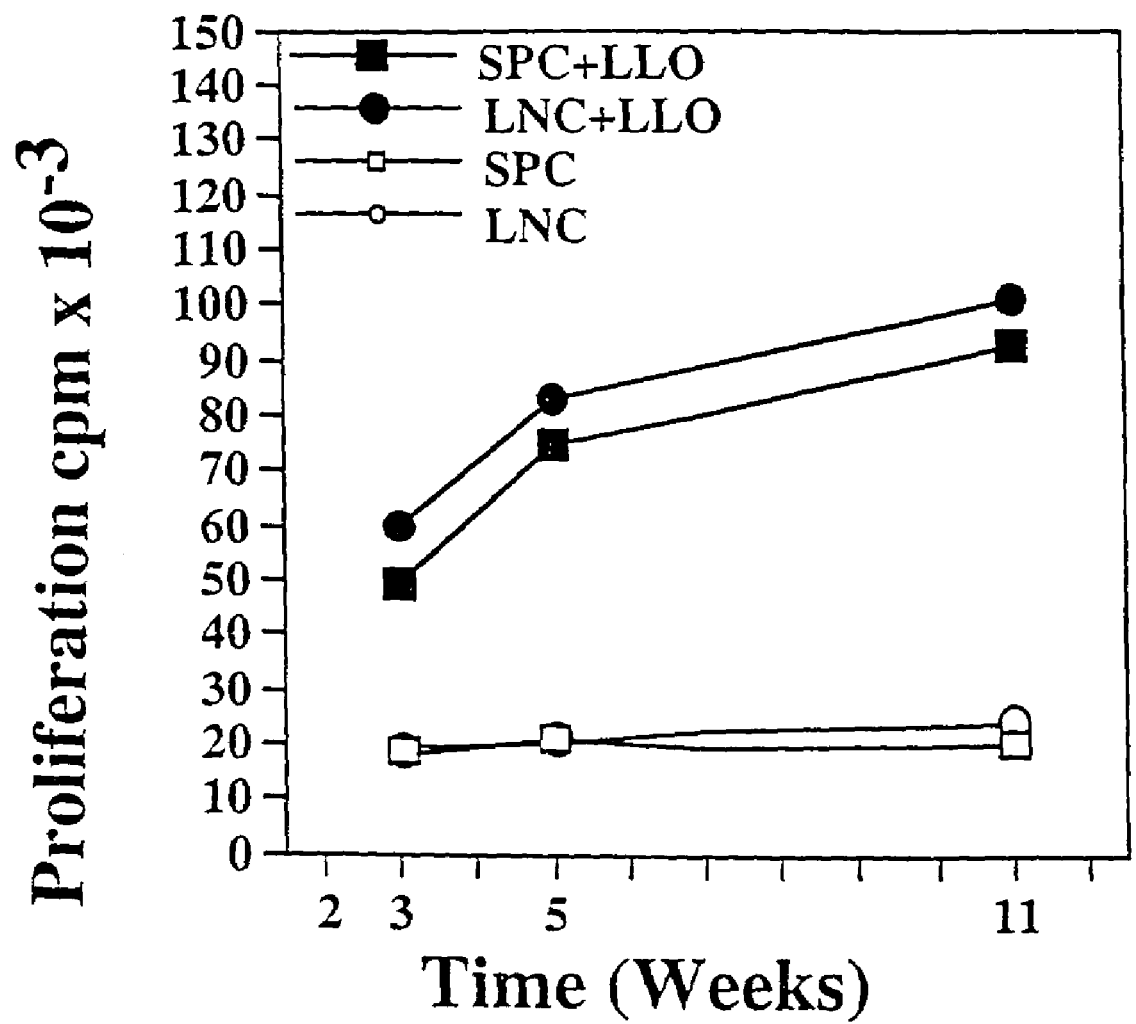
FIG 2C: Kinetic of proliferative response of spleen and lymph node cells from mice immunized once with pCMVhly.
Figure 2D:
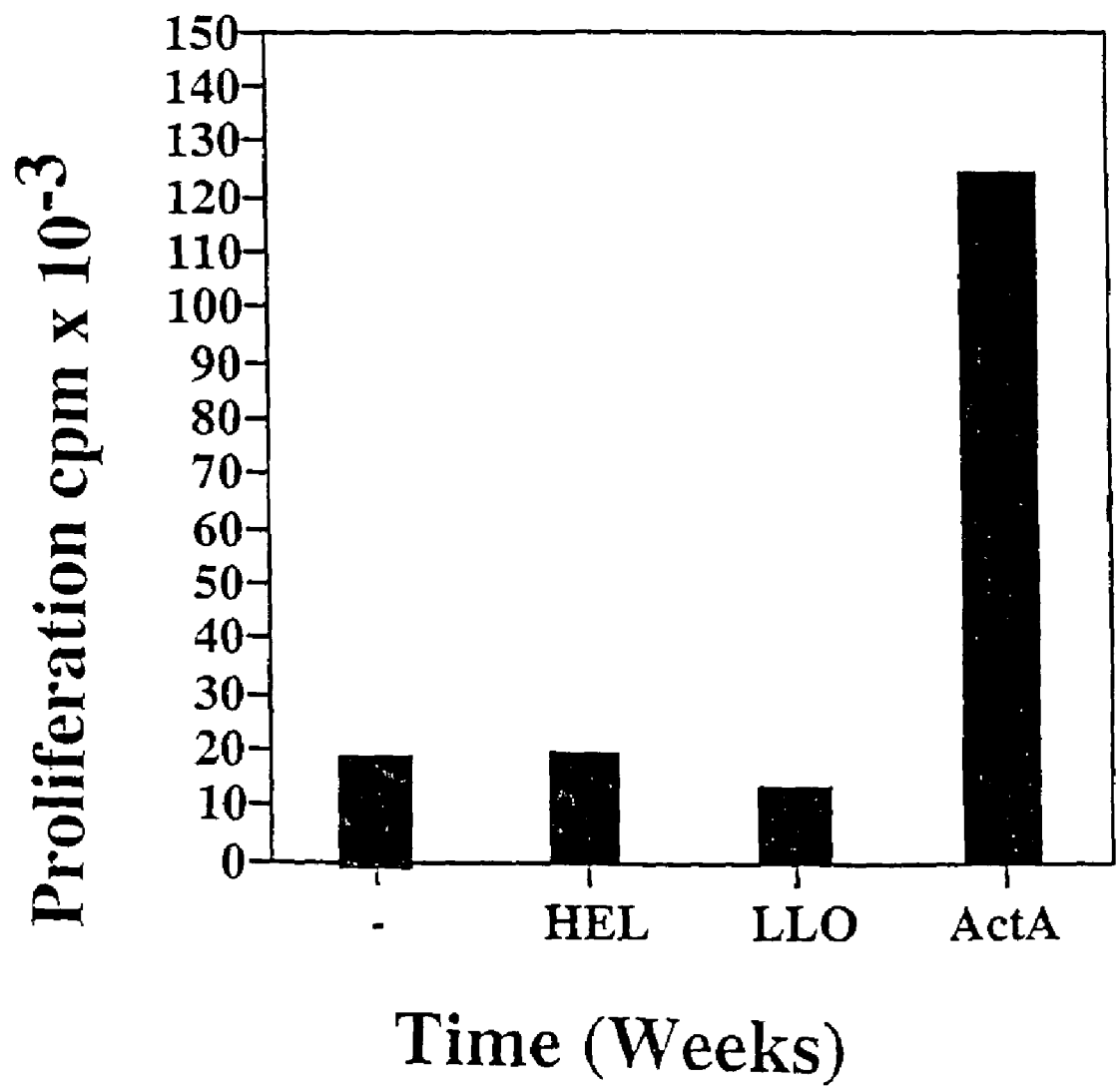
FIG. 2D: Specificity of proliferative response of spleen cells from mice immunized four times with pCMVActA. T cells tested were the same as those displayed in panel D at week 11. Similar results were obtained at other time points.
Figure 2E:
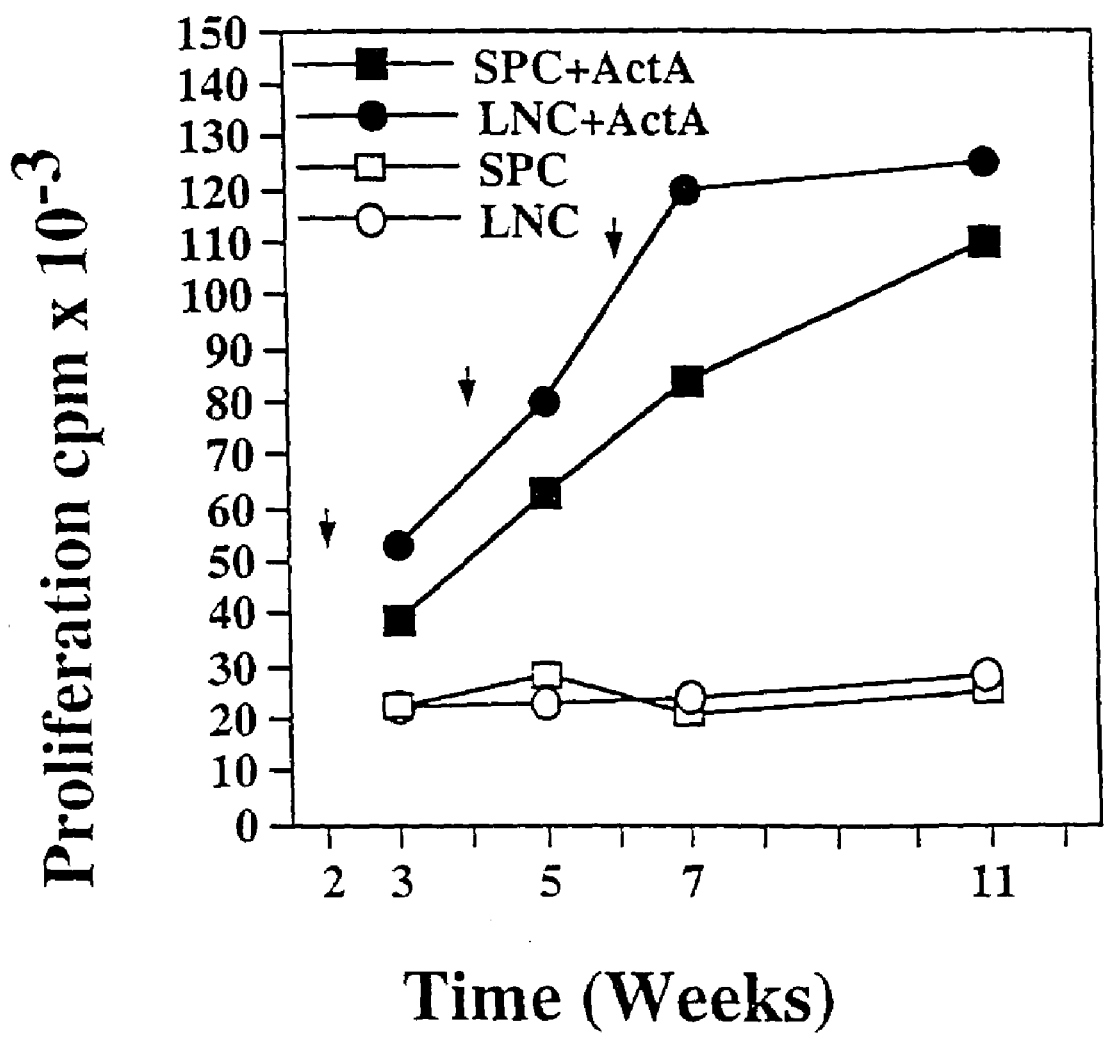
FIG. 2E: Kinetic of the proliferative response of spleen and lymph node cells immunized four times with pCMVActA. Arrows indicate booster immunizations.
Figure 2F:
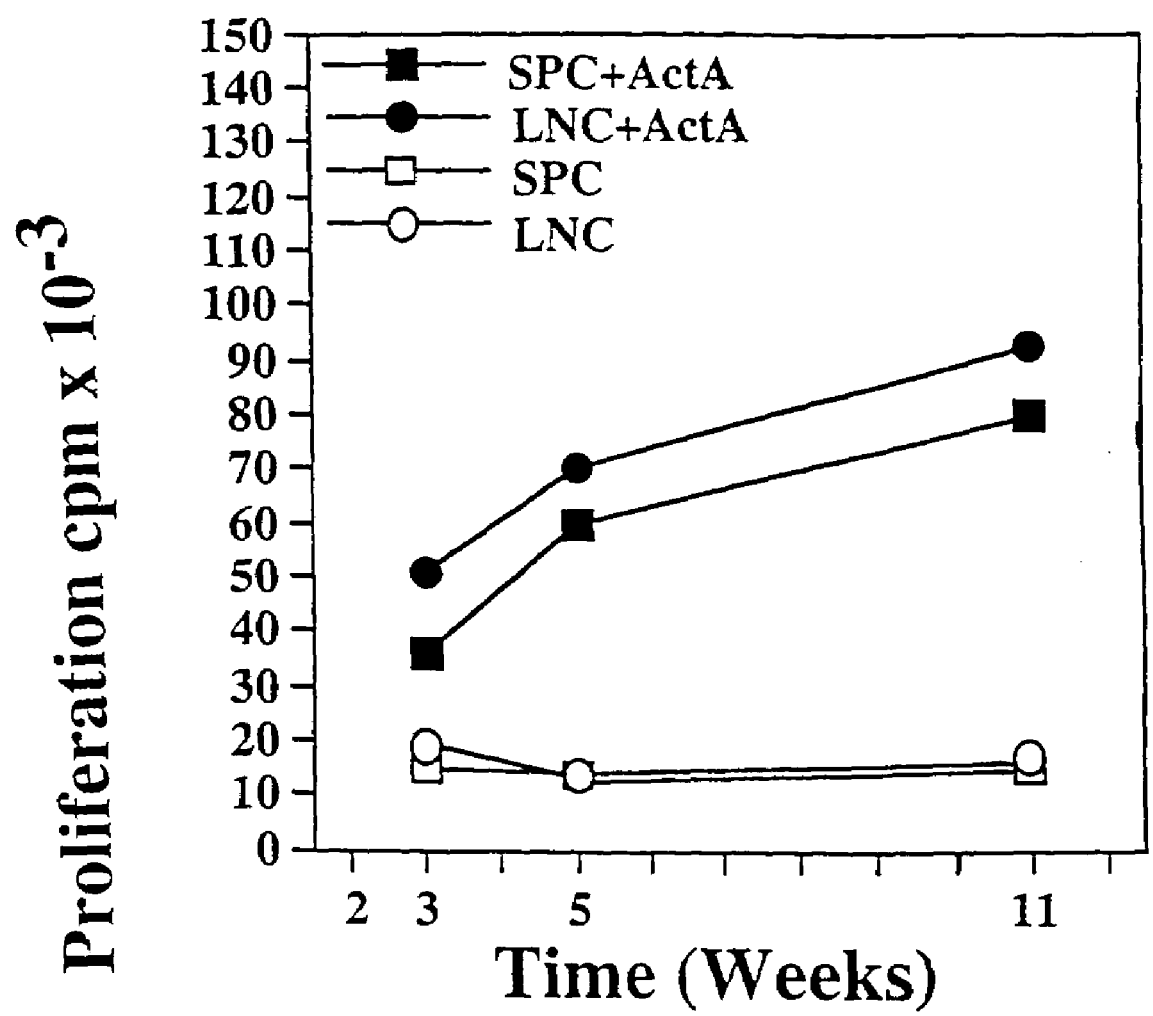
FIG. 2F: Kinetic of the proliferative response of spleen and lymph node cells from mice immunized once with pCMVActA. Similarly, spleen and lymph node cells from mice immunized with pCMVβ (β-gal) never reacted with either listeriolysin or ActA but could respond to restimmulation with β-gal (data not shown).
Figure 3A:
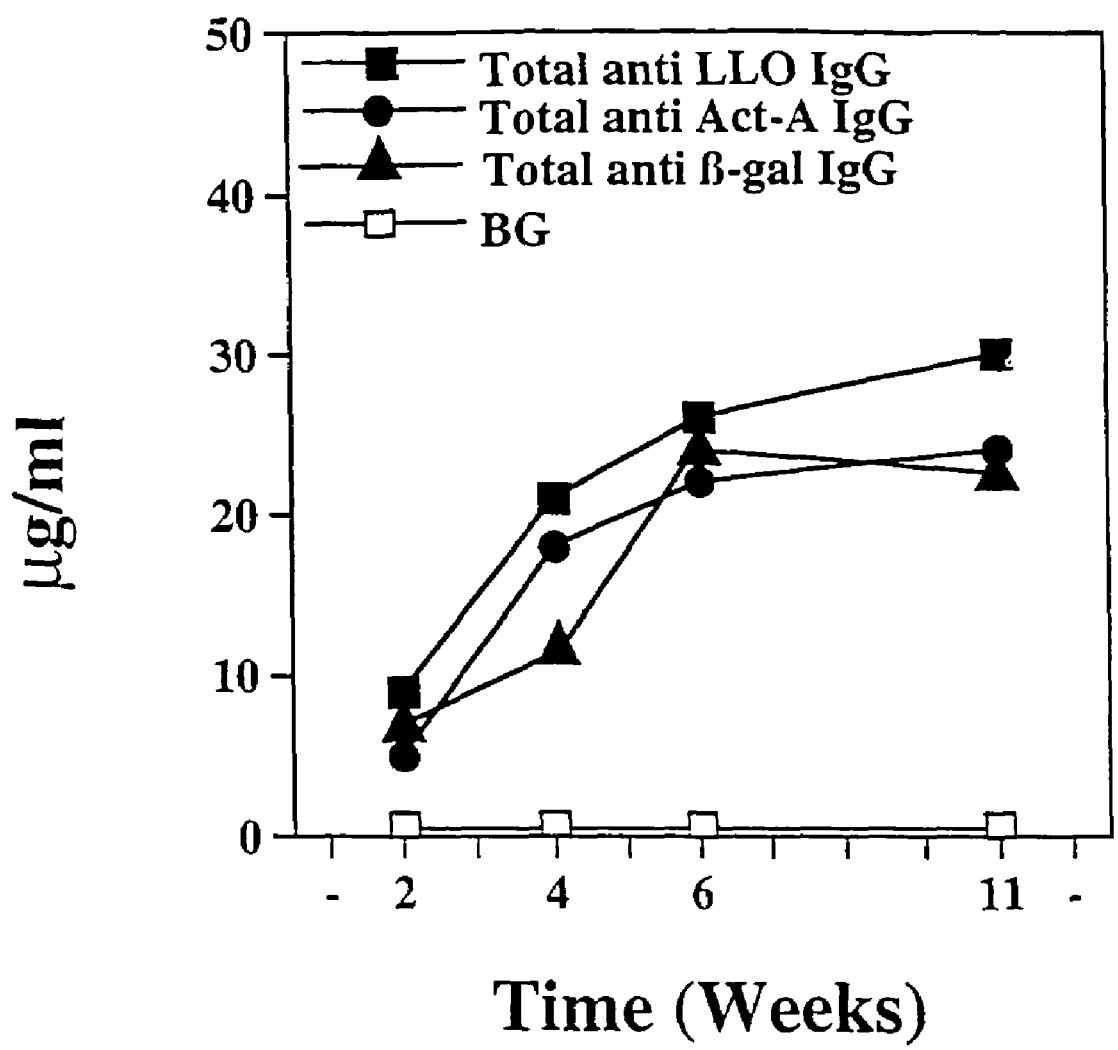
FIG. 3 Kinetics and subclass distribution of specific serum IgG from mice orally immunized with S. typhimurium aroA carrying eukaryotic expression plasmids which encode listeriolysin, ActA or β-gal. Sera from the same mice tested for cytotoxic and proliferative T cell responses displayed in FIGS. 1 and 2 were used and assayed in specific ELISA's. Mice were immunized four times (FIG. 3A) or once (FIG. 3B) with pCMVhly, pCMVActA or pCMVβ respectively, and pooled sera were tested for antigen specific serum IgG. To assess specificity all sera were tested on all three antigens. Reactivity was only observed against the immunizing antigen (data not shown). Identical results were obtained by immunoblotting using the same antigens (data not shown). The subclass distribution 11 weeks after the first immunization was determined from the sera of individual mice immunized four times (closed symbols) or once (open symbols) with either pCMVhly (FIG. 3C) or pCMVActA (FIG. 3D).
Figure 3B:
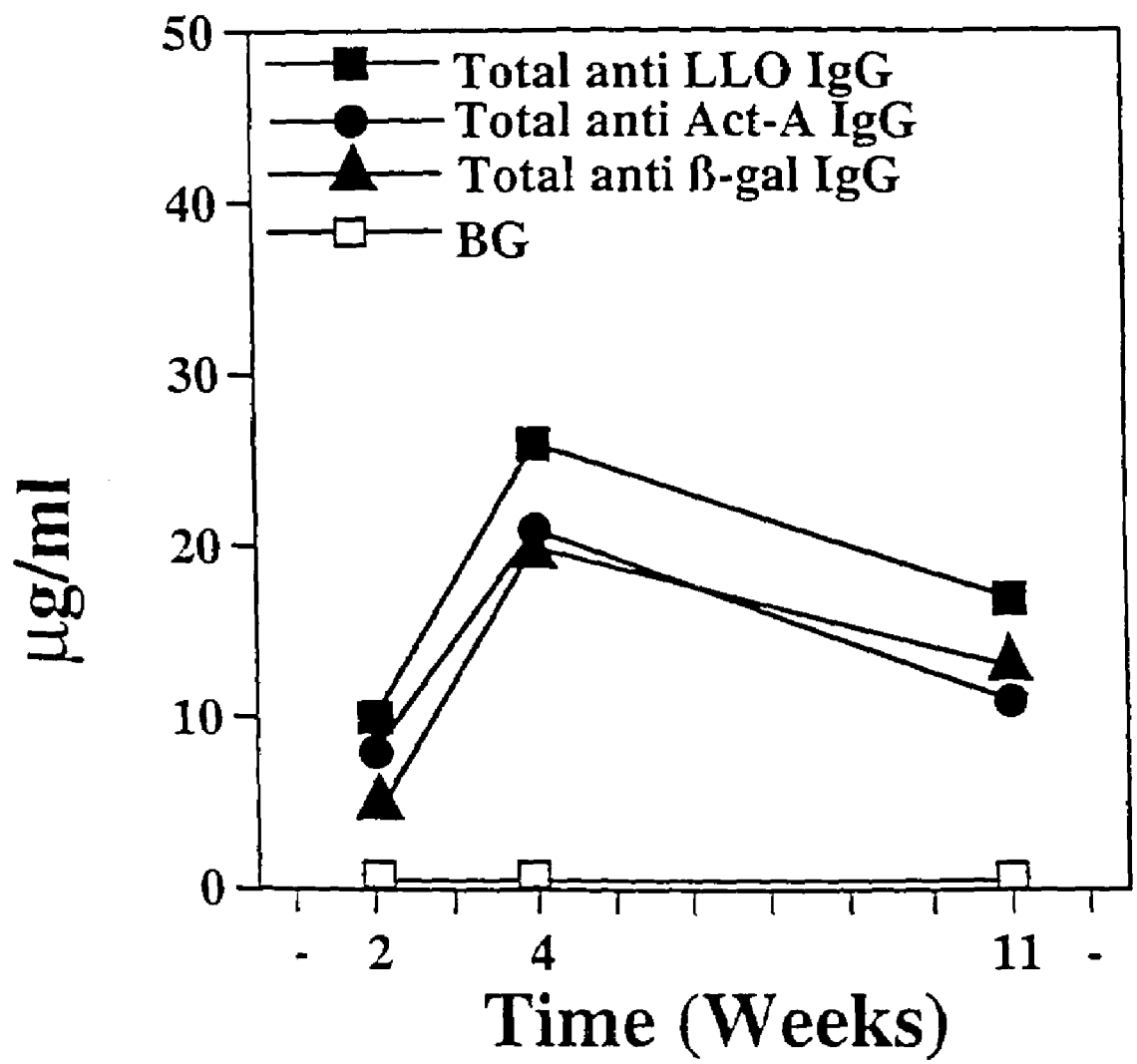
Figure 3C:
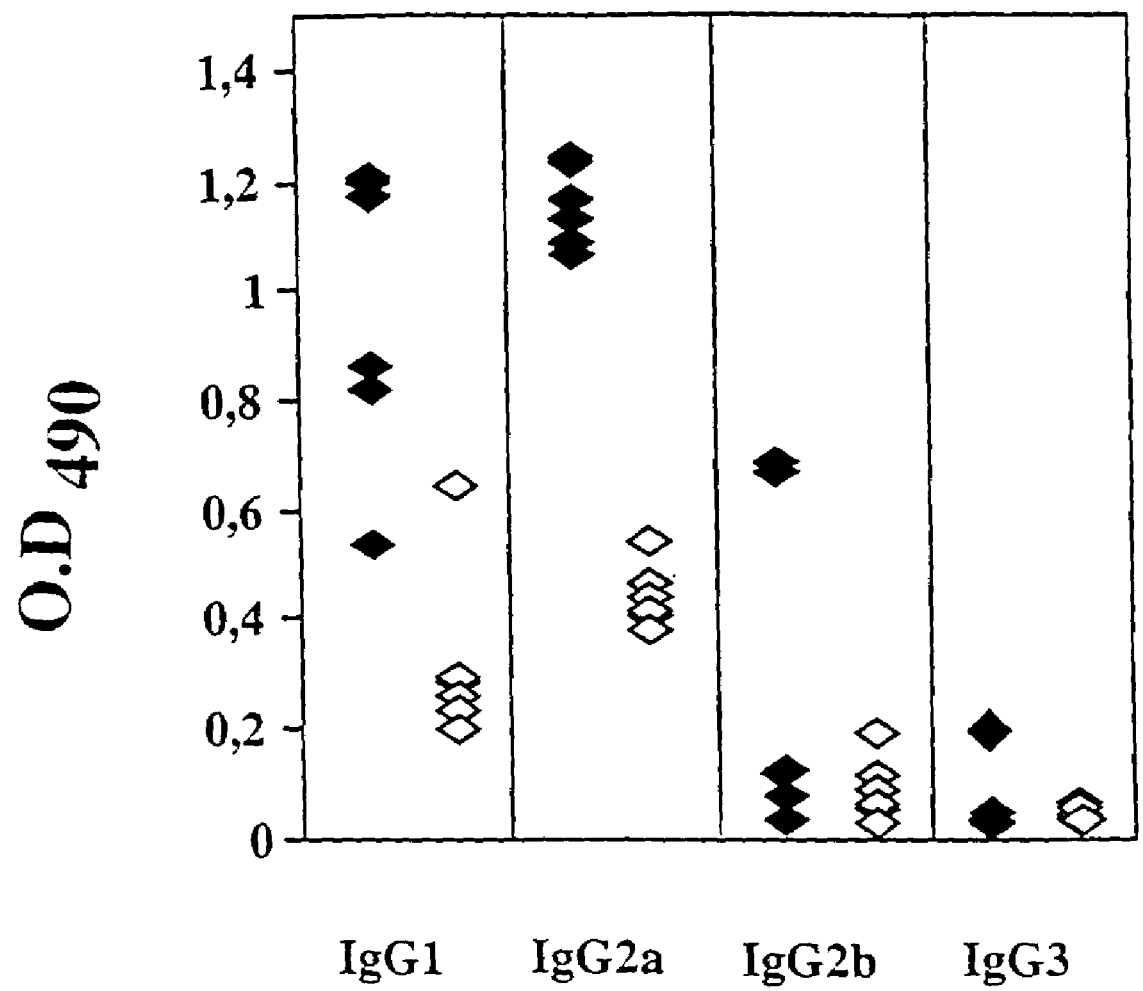
Figure 3D:
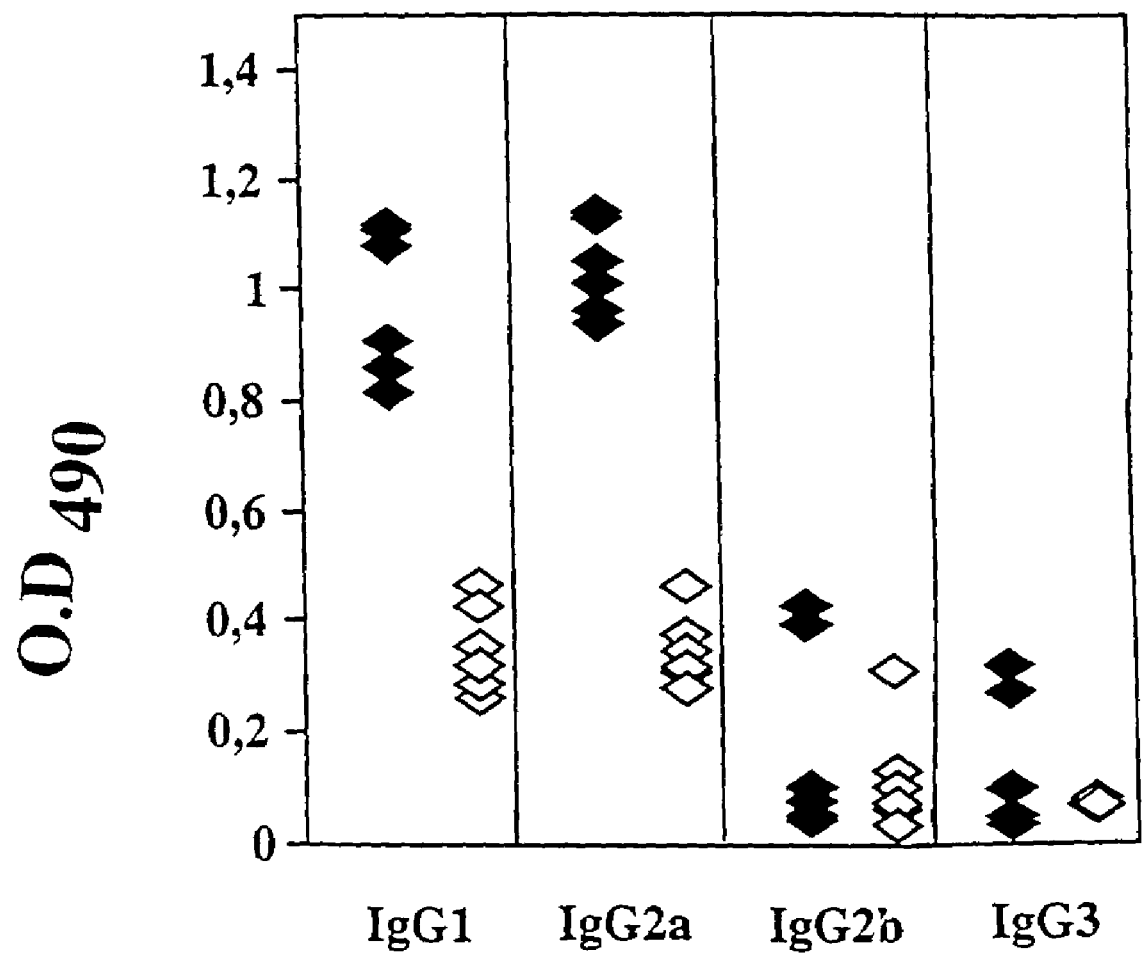
Figure 4A:
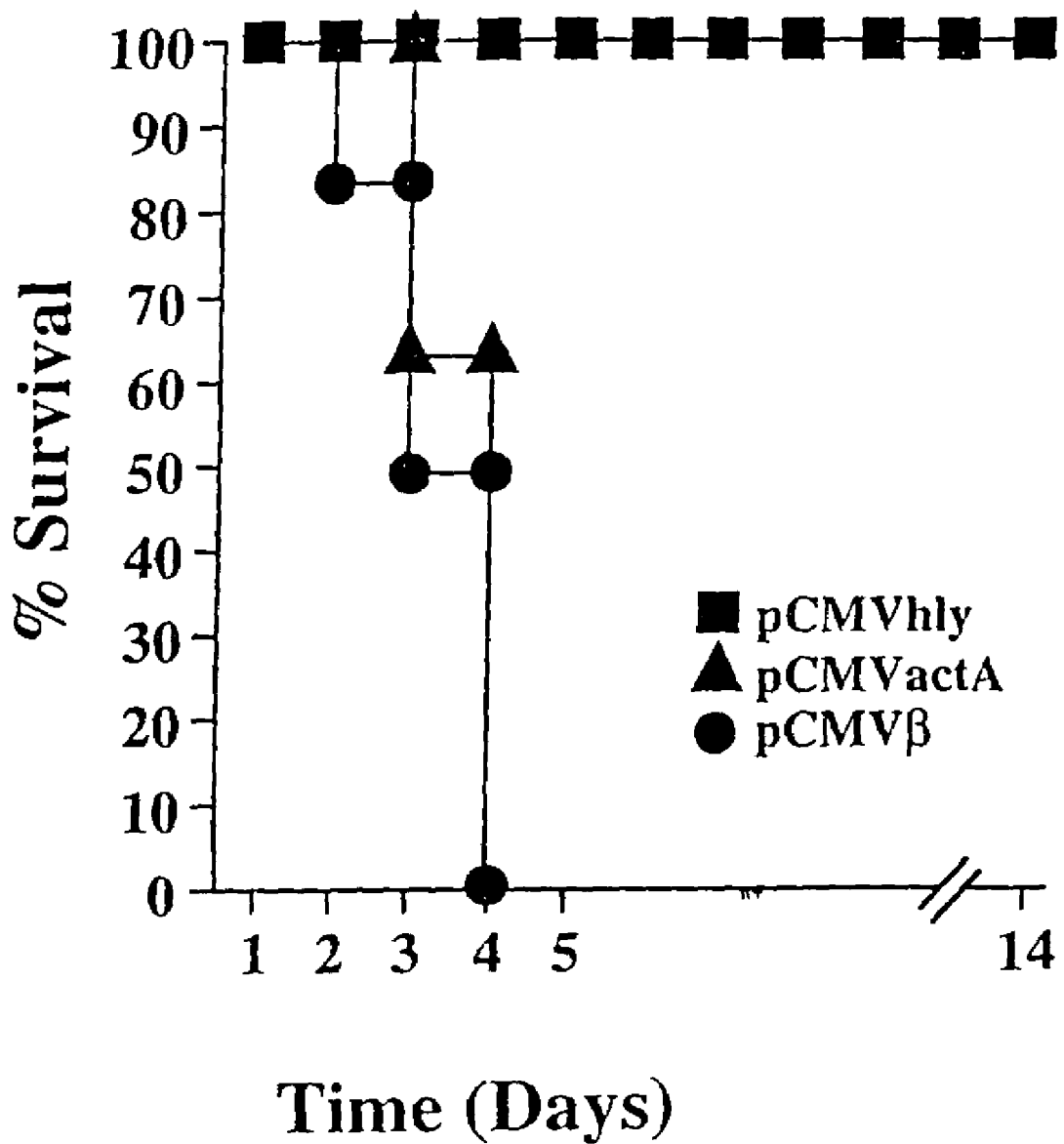
FIG. 4 Oral immunization with S. typhimurium aroA carrying the eukaryotic expression plasmid which encodes listeriolysin induces a protective immune response, whereas immunization with bacteria carrying the expression plasmid for ActA is not protective. Groups of six mice were immunized four times with two week intervals (FIG. 4A) or only once (FIG. 4B) with Salmonella carrying pCMVhly, pCMVActA or pCMVβ and challenged with a lethal dose of $5 \times 10^4$ L. monocytogenes EGD ($10 \times LD_{50}$) intravenously. Mice that had been immunized only once with pCMVhly became moribund after two days. However, four of them recovered and survived in good condition until the experiment was terminated two weeks later.
Figure 4B:
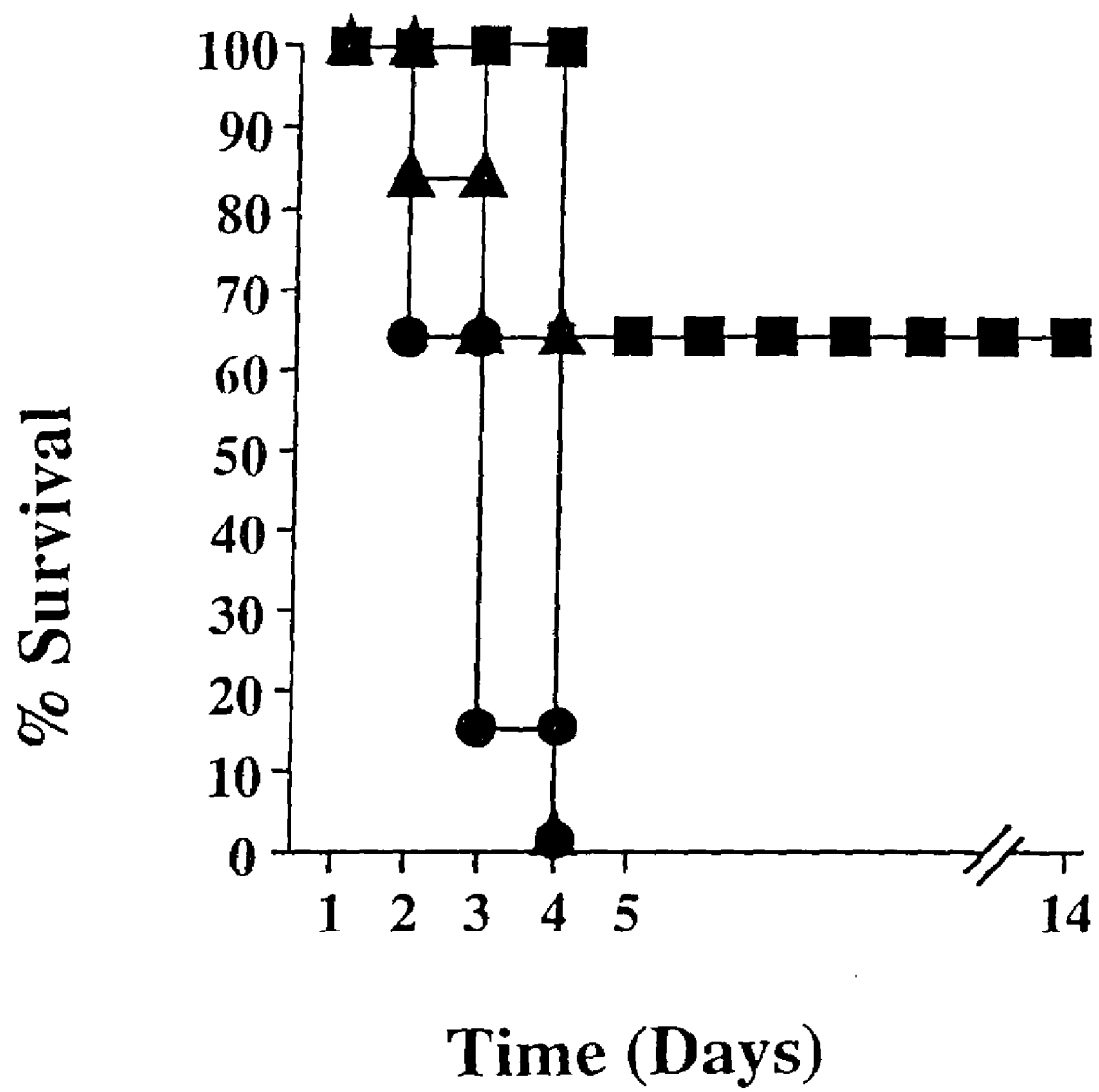
Figure 5A:
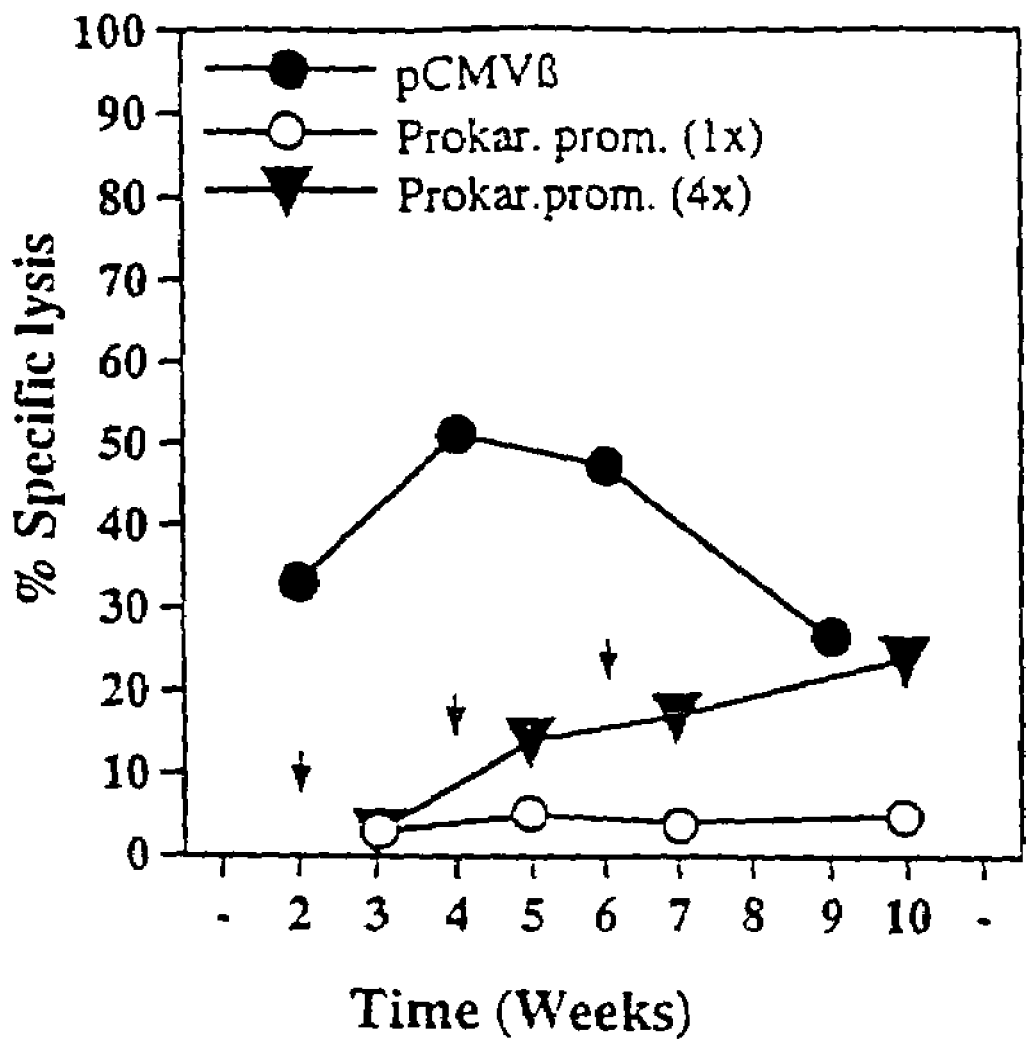
FIG. 5A. Cytotoxic response of restimulated spleen cells tested at an effector to target ratio of 10:1. The β-gal expressing transfectant P13.1 was used as target in the JAM assay.
Figure 5B:
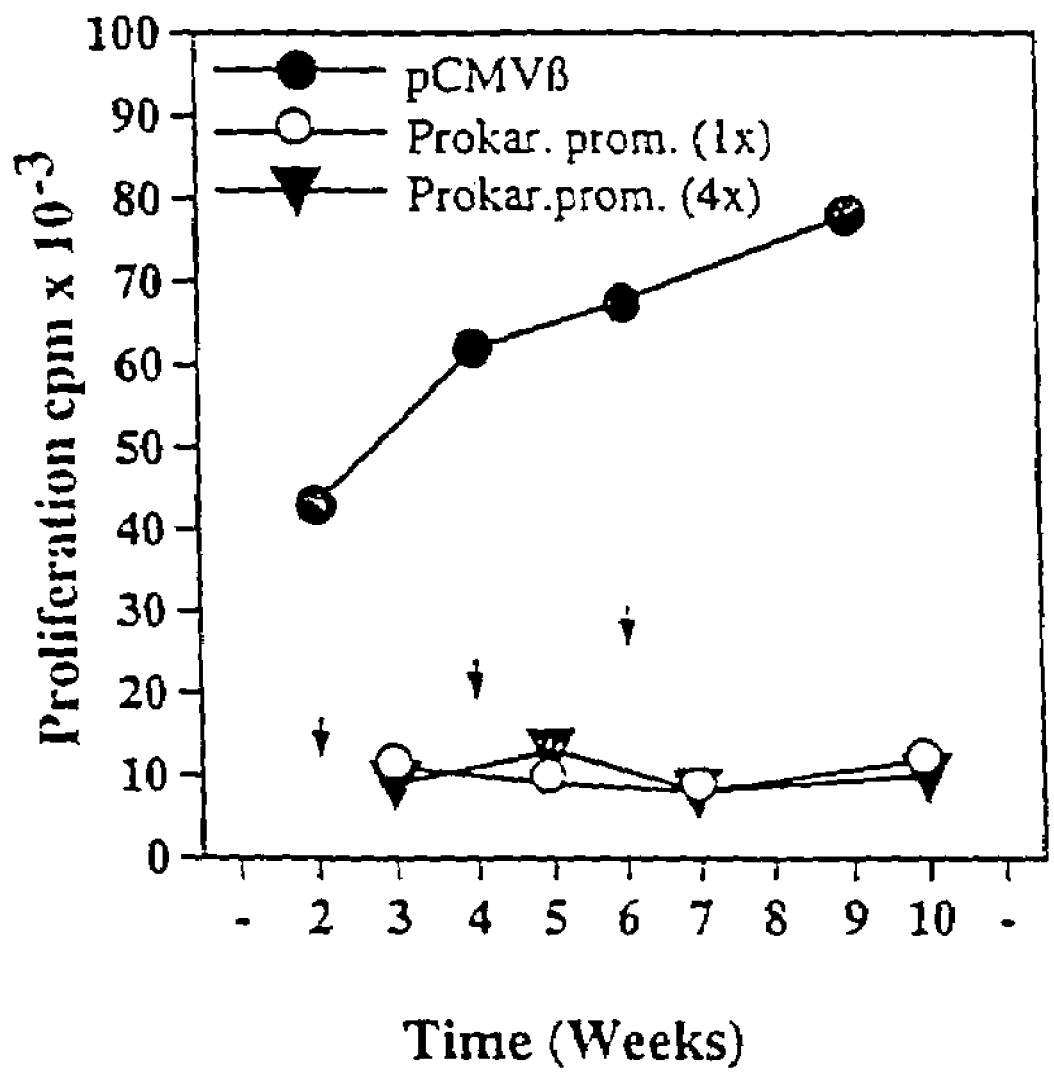
FIG. 5B. Proliferative helper T cell response of spleen cells with isolated b-gal as antigen.
Figure 5C:
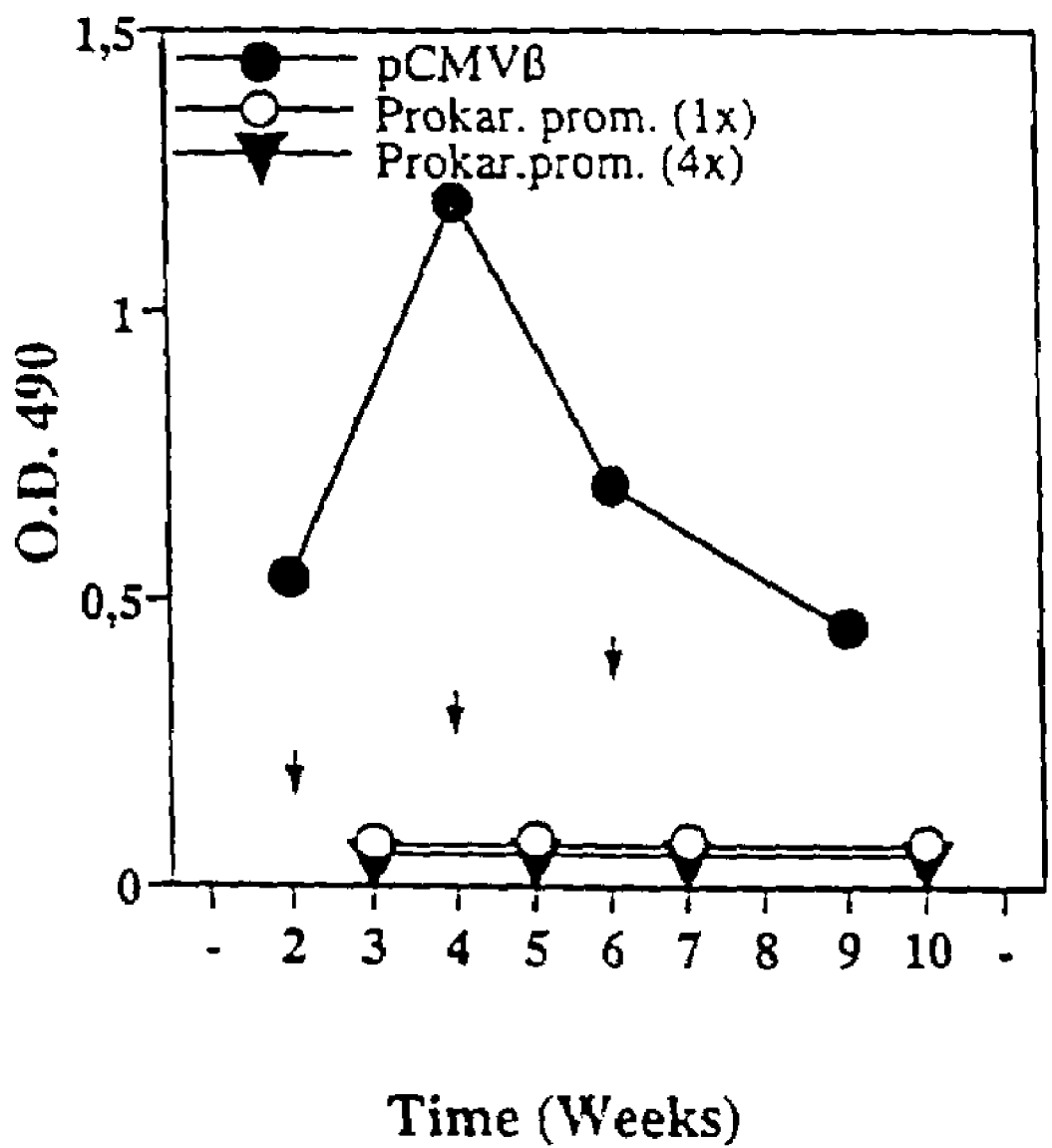
FIG. 5C: Antibody response against β-gal from pooled sera measured by ELISA. Data displayed in FIG. 5A–C were obtained with cells or sera from the same mice. All assays were performed as described in FIGS. 1–3.
Figure 6:
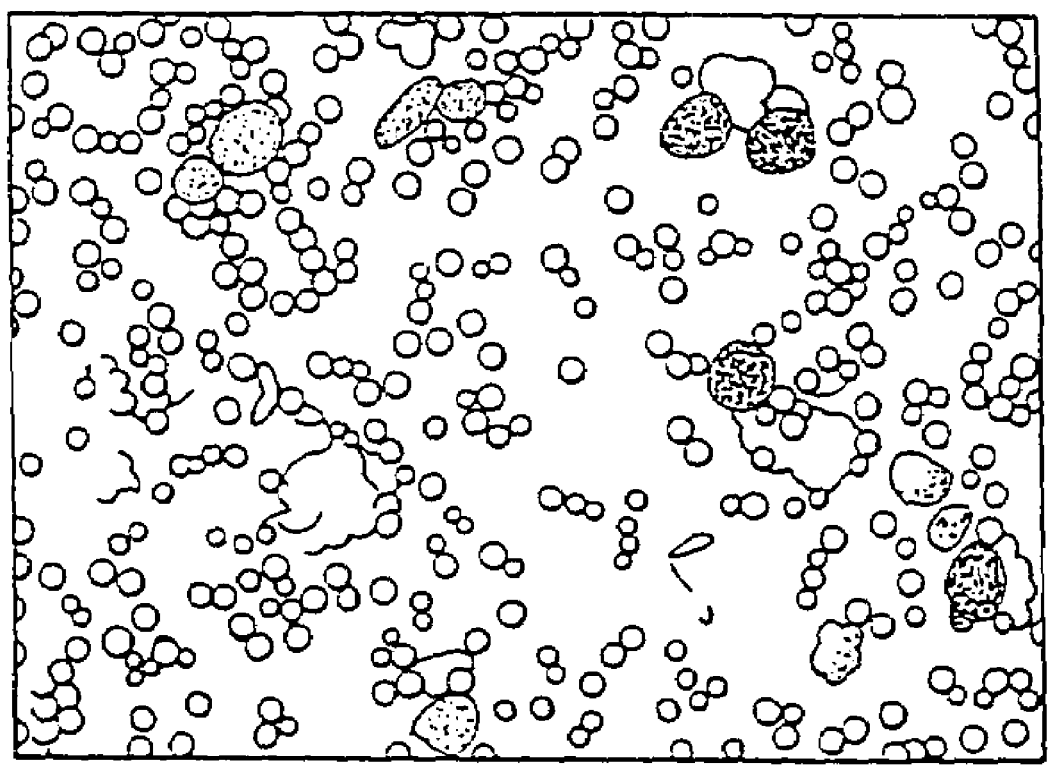
FIG. 6 Expression of enzymatic β-gal activity in peritoneal exudate cells after infection with S. typhimurium aroA that harbor an eukaryotic expression plasmid for β-gal. Freshly isolated peritoneal exudate cells (PECs) were allowed to adhere for two hours and infected at a MOI of 10 for 15 min with Salmonella bearing pCMVβ in antibiotic free medium. Following a wash and addition of gentamycin to kill bacteria which remained outside of the cells, incubation was continued for 3–4 h at 37 C. Medium was then supplemented with tetracycline to kill the bacteria by blocking their protein synthesis. After additional 24 h at 37 C cells were washed with PBS, dried, fixed with acetone/methanol and incubated overnight with the X-gal substrate. Sometimes, expression of β-gal activity in up to 30% of the adherent cell population was observed. Only macrophage-like cells expressed enzymatic activity. The small cells found in the displayed cultures most likely represent non-adherent lymphocytes which were not removed in this particular experiment. Tetracycline remained in the medium through the whole experiment. Staining the cells already after 4 h did not reveal any enzymatic activity.
Figure 7:
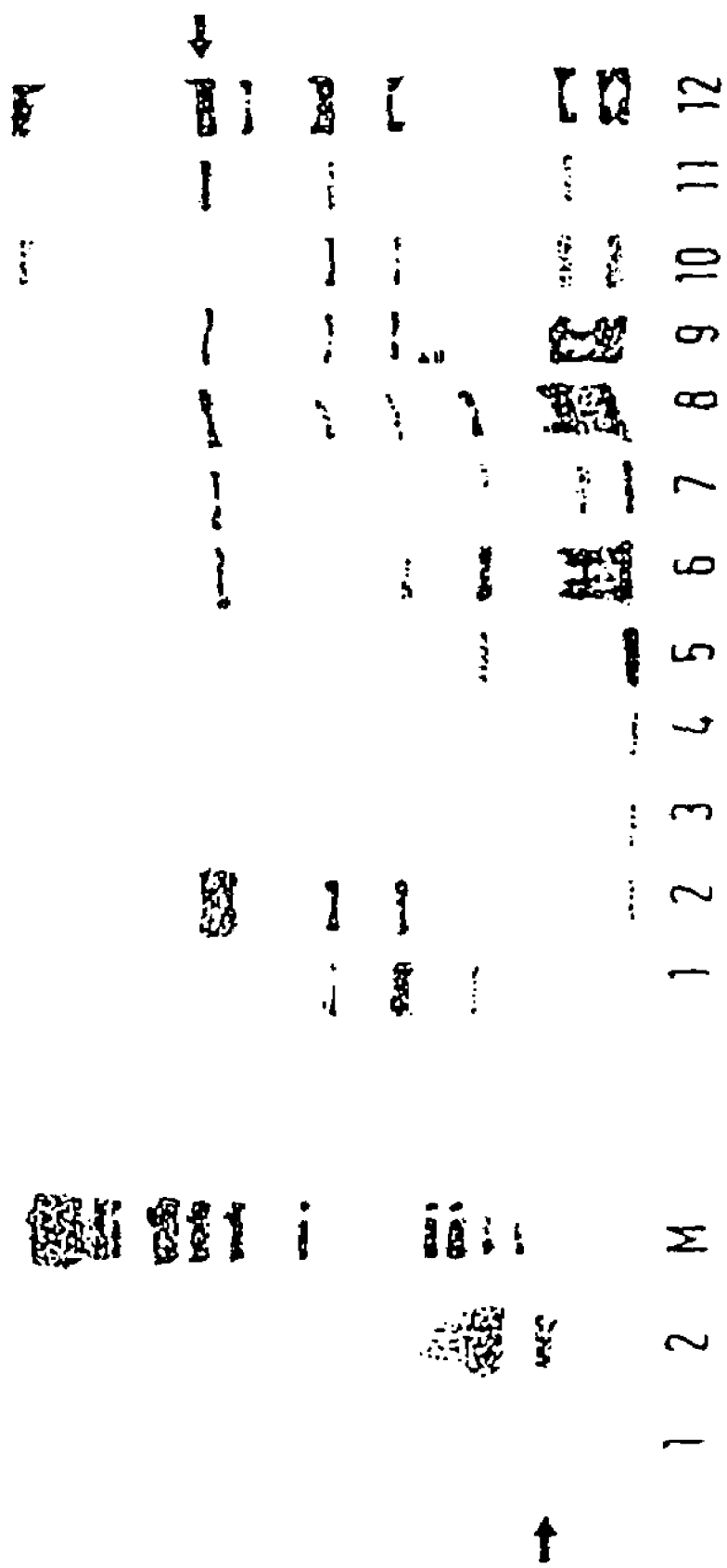
FIG. 7 The eukaryotic host cells transcribe and translate β-gal derived from S. typhimurium aroA harboring the expression plasmid. A: RNA derived from PEC's 24 h after infection with Salmonella carrying pCMVβ was analysed by RT-PCR. A primer pair that borders the splice donor and acceptors sites downstream of the promotor was used. In lane 2 a band of 196 bp (indicated by the arrow) could be detected. DNA sequencing identified this fragment as a splice product. The stronger 227 bp long fragment seen in this lane is either due to carry over of DNA into the RNA preparation or due to inefficient splicing. Lane 1 shows the untreated macrophage control and the lane marked M contains the molecular size marker used. Since the signal of the splice product was exrtremely weak we inverted the colours from white to black. This resulted in an increase of contrast and and allowed the visualization of the splice product on the graph. B: PEC's were infected with pCMVβ carrying Salmonella as described and after incubation at various length of time biosynthetic labelling was performed in the presence or absence of tetracycline followed by immunoprecipitation with β-gal specific monoclonal antibodies. Controls: (1) BHK cells; (2) BHK cells transfected with β-gal (positive control). Infected PEC'S: (3) incubated four hours post infection (p.i.), without tetracycline; (4) incubated four hours p. i., with tetracycline during labelling; (5) incubated four hours p.i., with tetracycline during incubation and labelling; (6) incubated 24 h p.i., without tetracycline; (7) incubated 24 hours p.i., with tetracycline during labelling; (8) incubated 24 h p.i., with tetracycline during incubation and labelling (9) incubated 48 h p.i., without tetracycline; (10) incubated 48 h p.i., with tetracycline during labelling, a 100-fold excess of β-gal over the precipitating antibody was added to the lysate before immunoprecipitation; (11) incubation of 48 h p.i., with tetracycline during labelling; (12) incubation 48 h p.i., with tetracycline during incubation and labelling. No specific band was observed after 4 h of incubation under any conditions. However, after allowing 24 h or more for a DNA transfer and expression to occur, a specific band for β-gal—indicated by the arrow—can be observed.
Figure 8:
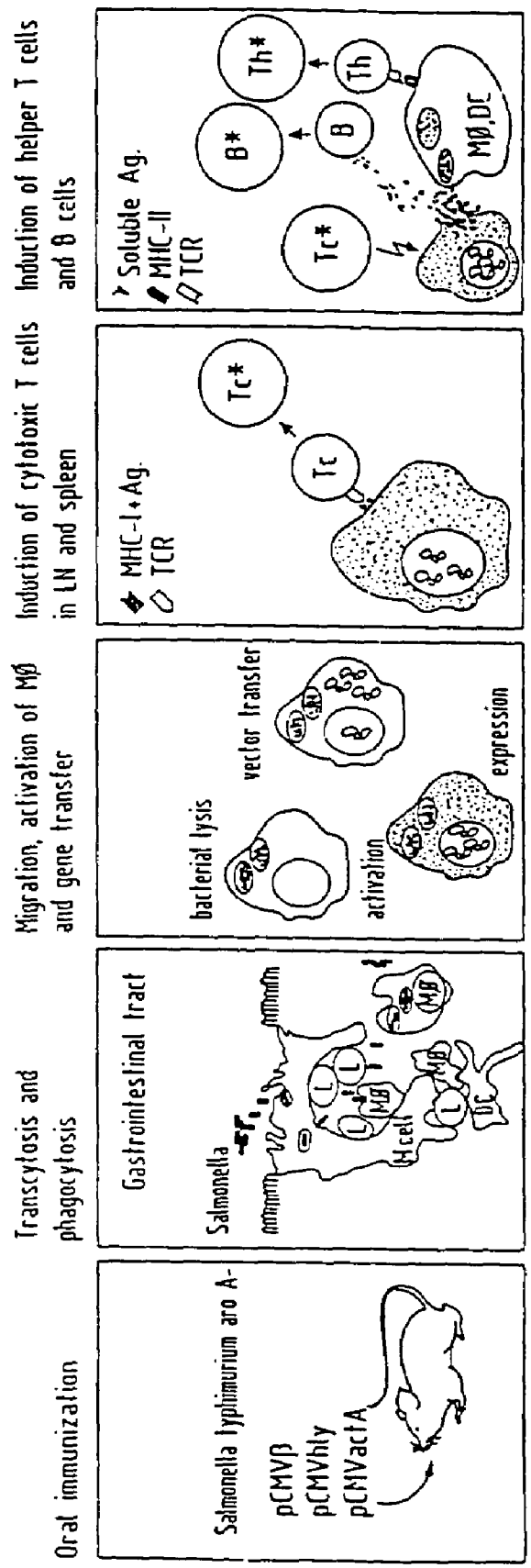
FIG. 8 Schematic representation of the sequence of events that might occur in vivo after oral genetic immunization with attenuated *S. typhimurium* aroA.

*Salmonella typhimurium* Strain LT2 cf.
   Hosieth & Stocker in Nature, 291 (1981) 238–239.
pCMVβ cf. Sizemore et al. in Science, 270 (1995) 299–302.
*Salmonella typhi* Ty21a cf. J. Infections Diseases, 131 (1975) 553.
actA gene cf. Domann in EMBO J., 11 (1992) 1981–1990.
hly gene cf. Mengaud et al. in Infection Immunity, 56 (1988) 766–772.
Expression screening cf. Mougneau et al. in Science, 268 (1995) 563–566; and
   Huynh et al. in Glover, DNA Cloning, Vol. 1: 49–78.

Experimental Procedures

Mice
   Female BALB/c (H-2$^d$) mice 6–8 weeks old, were obtained from Harlan Winkelmann (Borchem, Germany).

Media, Reagents and Antigens
   RPMI (Gibco), supplemented with 10% fetal bovine serum, where required, was used as culture medium for eukaryotic cells and all functional assays were performed in this medium. Solid and liquid Luria Bertani medium (LB, Sambrook) was used for growing *E. coli* and *S. typhimurium* strains. Brain heart infusion broth or agar (BHI; Difco, Detroit, USA) was used for growing *L. monocytogenes* EGD. Media were supplemented, where required with 100 μg/ml of ampicillin. Concanavalin-A (con-A), hen egg lysozyme (HEL), tetracycline, β-galactosidase of *E. coli.* potassium ferrocynide and potassium ferricynide were purchased from Sigma (Sigma, St. Louis, USA), listeriolysin was purified as described (Darji et al., 1995b). Soluble ActA protein (AA 31-505) was purified from supernatants of recombinant *L. monocytogenes* (Gerstel et al. to be published).

Bacterial Strains and Plasmids
   The *E. coli* strain XL1-Blue (Strategene, Heidelberg, Germany) was used as a host during the cloning experiments and to propagate plasmids. The auxotrophic *S. typhimurium* aroA strain SL7207 (*S. typhimurium* 2337-65 derivative hisG46, DEL407 [aroA:Tn10{Tc-s}]), kindly provided by Dr. B. A. D. Stocker, Stanford, Calif., USA, was used as a carrier for the in vivo studies. The hemolytic *L. monocytogenes* strain EGD (serotype 1/2a; Chakraborty et al., 1992) was used for in vivo protection assays and preparation of genomic DNA. The DNA was used as template for the PCR amplification of actA and hly genes. The eukaryotic expression vector pCMV, (Clontech, Palo Alto, USA) containing β-gal of *E. coli* was used for the cloning by replacing β-gal with the amplification products containing a truncated variant of actA or of hly. For expression of β-gal in *Salmonellae* the plasmid pAH97 was used (Holtel et al., 1992). It contains the Pr and Ps promotor of the Xyl S gene of *Pseudomanas putida* and results in constitutive expression of β-gal (384 U) in the *S. typhimurium* aro A strain. Bacterial cultures were grown at 37° C. and aerated by shaking at 200 r.p.m.

Recombinant DNA Techniques
   DNA preparation, genetic manipulations and PCR were carried out according to standard protocols (Sambrook et al., 1982), and plasmid DNA transformation of bacterial cells was performed as described by Hannahan or by electroporation (O'Callaghan and Charbit, 1990). DNA sequencing was performed using a Taq Dye Deoxy terminator cycle sequencing system (Applied Biosystems) and analyzed on an Applied Biosystems 373A automated DNA sequencer.

Cloning of ActA and Hly into the Eukaryotic Expression Vector pCMVb
   For the construction of the eukaryotic expression vector pCMVActA, a 1.8 kb fragment encoding AA 31 to 613 of a ActA polypeptide without the membrane anchor (Domann et al., 1992) was amplified by PCR using the forward and reverse primers:
   5'-ATAAGAAT<u>GCGGCCGC</u>CATGGCGACAGATAGC GAAGATTCTAGTC-3' (SEQ ID NO:1) and
   5'-ATAAGAAT<u>GCGGCCGC</u>TTACGTCGTATGGTTCC CTGGTTCTTC-3'; (SEQ ID NO:2) and genomic DNA from *L. monocytogenes* strain EGD as template. In a similar way recombinant plasmid pCMVhly was constructed. A 1.4 kb fragment encoding a non hemolytic variant comprising amino acids 26 to 482 of hly and deleting the peptide essential for hemolytic activity (Mengaud et al., 1988) was amplified using the forward and reverse primers:
   5'-ATAAGAAT<u>GCGGCCGC</u>CATGGATGCATCTGCA TTCAATAAAGAAAATTC-3' (SEQ ID NO:3) and
   5'-ATAAGAAT<u>GCGGCCGC</u>TTATTTAGCGTAAACA TTAATATTTCTCGCG-3'. (SEQ ID NO:4) PCR primers were designed in such a way that the resulting fragments contain NotI flanking restriction sites (underlined) and start and stop codons were introduced (ATG and TTA in bold). The PCR fragments were digested with NotI and ligated with NotI-digested pCMVβ, thereby generating pCMVActA and pCMVhly, respectively. The coding region for β-gal is deleted from pCMVb by the NotI digestion. The DNA sequence of the inserted PCR fragments were verified by Taq Dye Deoxy terminator cycle sequencing.

Immunization and Challenge

For immunization, groups of 5–10 female BALB/c mice were fed with 30 ml of 10% sodium bicarbonate buffer containing $10^8$ recombinant *S. typhimurium* aroA strain harboring one of the eukaryotic expression vectors pCMVβ, pCMVhly or pCMVActA or the prokaryotic β-gal expression plasmid pAH97 (Holtel et al., 1992). Mice received either a single immunization or four immunizations at 14 days intervals. Serum samples from both groups of mice were obtained on day −1, 7, 21, 35 and 63 and were stored at −20° C. until used in enzyme-linked immunosorbent assay (ELISA) or immunoblot. Mice of each group were sacrificed at weeks 3, 5, 7 and 11 after the first immunization and tested for T cell responses. For protection studies, immunized mice were challenged i.v. on day 90 (one and half month following the last boost of mice receiving multiple immunizations) with a lethal dose of $5 \times 10^4$ *L. monocytogenes* EGD. Survival of mice was followed until day 14 post-challenge.

CTL Assay

For the determination of induction of cytotoxic T cells the $JAM_s$ assay was performed (Matzinger P., 1991). Briefly, $3 \times 10^5$ target cells were incubated for 4 h with 5 µCi $^3$H-thymidine (Amersham), washed and co-cultured with the spleen cells isolated from mice immunized with *S. typhimurium* aroA strains, harboring the eukaryotic or prokaryotic expression vectors at different effector to target ratios. Spleen cells were either assayed straight ex vivo or after in vitro restimulation for 5 days. To test for LLO specific cytotoxic T cells, P815 target cells were sensitized with 1 µg/ml of LLO peptide AA 91-99 (Pamer et al., 1991). The ActA specific cytotoxicity was revealed by sensitizing the radiolabeled P815 cells with a mixture of 1 µg/ml purified hemolytically active LLO and 1 µg/ml of purified ActA protein for 30 min at RT. We have shown previously that it is possible to sensitize target cells very efficiently in vitro with soluble proteins by using the pore-forming activity of LLO. Target cells sensitized with LLO only were not lysed when T cells from mice that were immunized with *Salmonella* carrying the ActA expression plasmid were tested. This indicates that the assay is specific for ActA when mice were immunized with *Salmonellae* harboring ActA expression plasmids. To measure the β-gal specific cytotoxicity, P13.1—a P815 derivative transfected with the β-gal gene—was used as target cells (Rammensee et al., 1989). Mixtures of effector and target cells were incubated for 4–5 h at 37°, then plates were harvested on filtermats which finally were counted in a scintillation counter. All assays were performed in triplicates in 200 ml final volume in round bottom 96 well microtiter plates Proliferation Assay Induction of T helper cells was assayed by direct proliferation of cells isolated from spleens or lymph nodes of mice immunized with *S. typhimurium* aroA strains, harboring the eukaryotic expression vector pCMVβ, pCMVhly or pCMVActA or the prokaryotic β-gal expression vector pAH97. Proliferation of T cells were directly analysed by $^3$H-thymidine incorporation. Briefly, $2 \times 10^5$ T cells were co-cultured with $1 \times 10^5$ irradiated syngeneic spleen cells together with either 0.5 µg/ml purified LLO, 1 µg/ml Act-A or 1 µg/ml β-gal. After 48 h of incubation at 37° C., 1 mCi $^3$H-thymidine was added to each culture and after further 18 h of incubation, cells were harvested on filter mats and incorporation was counted in a scintillation counter. All experiments were performed in triplicates in 200 ml final volume in flat bottom 96 well microtiter plates.

ELISA

To evaluate the levels of immunoglobulins against LLO, Act-A and β-gal in serum specimens, 96-well ELISA plates (Maxisorp, Nunc) were coated with 0.5 µg/ml purified protein overnight at 4° C. Plates were washed three times with PBS/0.05% polyoxyethylene non-ionic detergent TWEEN 20 and then blocked with 3% BSA-PBS for 2 h at 37° C. Following two washes with PBS/0.05% polyoxyethylene non-ionic detergent TWEEN 20, serum samples if a 1:100 dilution were added to individual wells and incubated for 2–3 h at 37° C. Plates were washed above and biotinylated goat anti-mouse Ig (Dianova, Hamburg, Germany) in 1% BSA-PBS was added to each well and incubated for 1 h at 37° C. After three washes with PBS/0.05% polyoxyethylene non-ionic detergent TWEEN 20, horseradish peroxidase conjugated streptavidin (Dianova, Hamburg, Germany) in 1% BSA-PBS was added to each well and incubated for 1 h at 37° C. Plates were washed as above, developed with o-Phenylene diamine as substrate and measured in an ELISA reader at 490 nm. For antigen specific IgG subclasses determination, peroxidase conjugated goat anti mouse IgG1, IgG2A, IgG2b and IgG3 (Caltag laboratories, CA, USA) were used.

Detection of β-gal Activity

Expression of β-gal in host cells was monitored by incubating the fixed cells with the indicator substrate X-gal. Briefly, isolated peritoneal macrophages were allowed to adhere for a couple of hours at 37° C. in 24 well-plate in antibiotic free medium. After removing the non-adherent cells and washing with antibiotic free medium, *S. typhimurium* aroA, harboring the eukaryotic expression vector pCMVβ were added to the cells at a MOI of 10 and incubated at 37° C. for 15–30 min. Cells were washed again and bacteria remaining extracellular were killed by addition of medium containing 50 µg/ml gentamicin. Following 4 h of incubation at 37° C., 10 µg/ml of tetracycline was added to some of the cultures to block the intracellular bacterial multiplication and incubation was continued for further 24 h. This second antibiotic step was later found to be unnecessary because strains harboring the aroA mutation survive only for brief periods of time in these cells (data not shown). After 2–3 washes with PBS, cells were fixed with acetone/methanol (1:1 v/v) and freshly prepared X-gal substrate (5 mM potassium ferrocynide, 5 mM potassium ferricynide, 2 mM $MgCl_2$ and 100 mg/ml X-gal in PBS) was added. After overnight incubation at 37° C. β-gal expressing cells were detected by light microscopy. Quantitation of β-gal enzymatic activity in recombinant bacteria was determined according to standard procedures (Sambrook et al., 1982). Background (4U) was substracted from the experimental values.

RNA Isolation and RT-PCR

In order to test for expression of β-gal transferred into the eukaryotic host cells via *Salmonella*, the mRNA was probed for the presence of splice products derived from the splice donor and acceptors of the expression plasmid. To this end, PECs were infected in vitro at an MOI of 10 with *S. typhimurium* aroA harboring the eukaryotic expression vector pCMBβ and RNA was extracted as described (Chomczynski and Sacchi, 1987). RT-PCR of isolated RNA was performed. Briefly, 10 µg of isolated total cellular RNA was resuspended in 20 µl of DEPC-H$_2$O and incubated for 5 min at 70° C. with 10 µl of buffer containing 6 µl of reverse transcriptase buffer (250 mM Tris-HCl, 375 mM KCl, 15 mM MgCl$_2$); 0.4 mM dNTPs; 0.05 U random hexamers (Pharmacia, Uppsala, Sweden); and 1 mM DTT. Samples were spun down for 2 min at 15,000 rpm and 40 U RNAsin ribonuclease inhibitor (Promega) together with 200 U Superscript reverse transcriptase (Gibco, BRL) were added. RNA was reverse transcribed for 445 min at 37° C. and the reaction was stopped by heating the samples at 95° C. for 1 min followed by a short incubation on ice. Subsequently 500 ng of cDNA product was amplified by PCR in a final volume of 50 µl containing 0.2 mM dNTP, 20 mM DTT, 3 µM of each of the 5' and 3' primer, 5 µl of 10× PCR buffer (100 mM Tris-HCl pH 9.0, 500 mM KCl, 1% gelatine, 1.5 mM MgCl$_2$, 1% polyoxyethylene non-ionic detergent TRITON X-100) and 5 U AmpliTaq-DNA-polymerase (Perkin Elmer). PCR was performed with an initial denaturation step of 10 min at 85° C. followed by 35 cycles of 20 sec denaturation at 95° C., 30 sec annealing at 60° C. and 30 sec extension at 72° C. The amplification products were visualized under an UV lamp after electrophoresis of a 15 µl aliquot of the reaction mixture on a 2% (w/v) agarose gel containing 0.5 µg/ml of ethidium bromide. The primer pair was designed in such a way that the presence of splice products should be indicated by a 190 bp and/or a 125 bp fragment The identity of the resumable splice product was confirmed by sequencing the fragments after isolation on a preparative agarose gel. The primer paid used for amplification and sequencing—SV40 forward:

5'GGATCCGGTACTCGAGGAAC-3' (SEQ ID NO:5), SV40 reverse: 5'-GCTTTAGCAGGCTCTTTCG-3' (SEQ ID NO:6).

Immunoprecipitations

Biosynthetic labeling of proteins in the presence of tetracycline followed by immunoprecipitation should only reveal protein expression by eukaryotic host cells. Therefore, 5×10$^5$ adherent PECs were infected for 30 min at 37° C. with ca. 5×10$^6$ *S. typhimurium* aroA harboring the eukaryotic expression vector pCMVβ in antibiotic free medium. After a thorough wash and further 4 h of incubation at 37° C., medium was supplemented with antibiotics or not and left at 37° C. for various periods of time before biosynthetic labeling. After two washes in PBS and 30 min starvation in methionine-free medium, cells were pulsed with 100 µCi [$^{35}$S]methionine for 2 h. Then cells were carefully washed and lysed in 0.5 ml ice cold lysis buffer (0.5% NP-40, 50 mM Tris-HCl, pH 7.4, 5 mM MgCl$_2$, 1 mM PMSF). After 45 min on ice, cells were centrifuged to remove nuclei and cell debris, and incubated at 4° C with 4 µg of anti-β-gal antibodies (Promega) for 30 min. Immune complexes were precipitated with protein A sepharose in 0.5% NP-40, 50 mM Tris-HCl pH 7.4, 5 mM MgCl$_2$ and 0.5 mM NaCl washed several times with the same buffer and analysed on 8% SDS-PAGE followed by fluorography. Into some samples a 100-fold excess of β-gal protein was added before addition of anti-β-gal antibodies to determine the specificity of the precipitation.

What is claimed is:

1. An attenuated *Salmonella* strain comprising a eukaryotic expression vector, wherein said vector comprises a eukaryotic promoter and a heterologous DNA encoding a heterologous polypeptide, wherein said DNA is under the control of said eukaryotic promoter, wherein the attenuation is suitable for administration to a vertebrate, and wherein said administration to said vertebrate of said attenuated *Salmonella* strain results in expression of said polypeptide by said vertebrate and generates an immune response by said vertebrate to said polypeptide.

2. The *Salmonella* strain of claim 1, wherein the strain is a *S. typhimurium* strain.

3. The *S. typhimurium* strain of claim 2, wherein the strain is selected from the group consisting of *S. typhimurium* aroA SL 7207, *S. typhimurium* LT2, and *S. typhimurium* aroA544 (ATCC Accession No. 33275).

4. The *Salmonella* strain of claim 1, wherein the strain is a *S. typhi* strain.

5. The *S. typhi* strain of claim 4, wherein the strain is *S. typhi* Ty21a.

6. The *Salmonella* strain of claim 1, wherein the eukaryotic expression vector comprises:
   a) a structural gene of β-galactosidase (β-gal) under the control of a human cytomegalovirus (CMV) immediate early promoter,
   b) a splice donor,
   c) two splice acceptor sites between the promoter and the β-galactosidase gene, and
   d) a polyadenylation site of SV40.

7. The *Salmonella* strain of claim 1, wherein the polypeptide is selected from the group consisting of an *Escherichia coli* β-galactosidase, a non-hemolytic truncated *Listeria monocytogenes* listeriolysin, and a truncated *Listeria monocytogenes* actA polypeptide.

8. A vaccine comprising the *Salmonella* strain of claim 1.

9. The *Salmonella* strain of claim 1, wherein the encoded polypeptide is capable of inducing an antibody response and a T-cell response, wherein the T-cell response comprises production of CD8 T-cells and CD4 T-cells.

10. The *Salmonella* strain of claim 1, wherein the encoded polypeptide is capable of inducing an antibody response and a T-cell response, wherein the antibody response comprises production of IgG1, IgG2, and IgA antibodies.

11. The *Salmonella* strain of claim 1, wherein the vertebrate is a human.

12. The *Salmonella* strain of claim 1, wherein the *Salmonella* strain is orally administered.

13. The *Salmonella* strain of claim 10, wherein the antibody response is induced after a single immunization.

14. The *Salmonella* strain of claim 9, wherein the T-cell response is induced after a single immunization.

15. The *Salmonella* strain of claim 7, wherein the polypeptide is a non-hemolytic truncated *Listeria monocytogenes* listeriolysin polypeptide.

* * * * *

```
                           SEQUENCE LISTING

<160> NUMBER OF SEQ ID NOS:  6

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 1
ataagaatgc ggccgccatg gcgacagata gcgaagattc tagtc              45

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 2
ataagaatgc ggccgcttac gtcgtatggt tccctggttc ttc                43

<210> SEQ ID NO 3
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 3
ataagaatgc ggccgccatg gatgcatctg cattcaataa agaaaattc          49
```

```
<210> SEQ ID NO 4
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 4
ataagaatgc ggccgcttat ttagcgtaaa cattaatatt tctcgcg                47

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 5
ggatccggta ctcgaggaac                                              20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 6
gctttagcag gctctttcg                                               19
```